(12) United States Patent
Addison et al.

(10) Patent No.: US 11,978,205 B2
(45) Date of Patent: May 7, 2024

(54) TEMPERATURE MONITORING WITH A THERMAL CAMERA

(71) Applicant: Covidien LP, Mansfield, MA (US)

(72) Inventors: Paul S. Addison, Edinburgh (GB); Philip C. Smit, Hamilton (GB); Anthony P. Addison, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 18/306,929

(22) Filed: Apr. 25, 2023

(65) Prior Publication Data

US 2023/0267609 A1 Aug. 24, 2023

Related U.S. Application Data

(62) Division of application No. 17/080,506, filed on Oct. 26, 2020, now Pat. No. 11,669,962.

(51) Int. Cl.
*G06T 7/00* (2017.01)
*G06T 7/90* (2017.01)
(Continued)

(52) U.S. Cl.
CPC .............. *G06T 7/0012* (2013.01); *G06T 7/90* (2017.01); *G16H 10/60* (2018.01); *G16H 40/67* (2018.01);
(Continued)

(58) Field of Classification Search
CPC ................. G06T 7/0012; G06T 7/90; G06T 2207/10048; G06T 2207/30201;
(Continued)

(56) References Cited

U.S. PATENT DOCUMENTS 7,340,293 B2 3/2008 Mcquilkin
8,918,162 B2 12/2014 Prokoski
(Continued)

FOREIGN PATENT DOCUMENTS

CN 106725358 A 5/2017
CN 111579083 A 8/2020
(Continued)

OTHER PUBLICATIONS

International Search Report and Written Opinion of International Application No. PCT/US2021/071993, dated Apr. 11, 2022, 16 pp.
(Continued)

*Primary Examiner* — Gabriel I Garcia
(74) *Attorney, Agent, or Firm* — Fletcher Yoder, P.C.

(57) ABSTRACT

An example system includes a thermal camera, a memory, and processing circuitry coupled to the thermal camera and the memory. The processing circuitry is configured to acquire a core temperature of a patient and acquire a first thermal image associated with the patient. The processing circuitry is configured to determine, based on the first thermal image, a first sensed temperature of a location associated with the patient. The processing circuitry is configured to determine a core temperature delta between the core temperature and the first sensed temperature. The processing circuitry is configured to acquire a second thermal image associated with the patient. The processing circuitry is configured to determine, based on the second thermal image, a second sensed temperature. The processing circuitry is configured to determine, based on the second sensed temperature and the core temperature delta, a measure of the core temperature.

10 Claims, 15 Drawing Sheets

(51) Int. Cl.
  *G16H 10/60* (2018.01)
  *G16H 40/67* (2018.01)
  *G16H 50/20* (2018.01)
  *G16H 50/30* (2018.01)

(52) U.S. Cl.
  CPC ............. *G16H 50/20* (2018.01); *G16H 50/30* (2018.01); *G06T 2207/10048* (2013.01); *G06T 2207/30201* (2013.01)

(58) Field of Classification Search
  CPC ........ G16H 40/67; G16H 10/60; G16H 50/30; G16H 50/20
  USPC ......................................................... 382/128
  See application file for complete search history.

(56) References Cited

U.S. PATENT DOCUMENTS

| | | | |
|---|---|---|---|
| 9,672,426 | B2 | 6/2017 | Chiang et al. |
| 9,750,414 | B2 | 9/2017 | Lane et al. |
| 9,918,644 | B2 | 3/2018 | Linné |
| 10,502,629 | B2 | 12/2019 | Johnson |
| 10,909,835 | B1* | 2/2021 | Singh .................. G01J 5/53 |
| 10,976,806 | B1 | 4/2021 | Vancamberg et al. |
| 2012/0316459 | A1* | 12/2012 | Abreu ................. A61B 5/01 600/549 |
| 2013/0215928 | A1 | 8/2013 | Bellifemine |
| 2013/0235901 | A1 | 9/2013 | Shin |
| 2015/0051461 | A1* | 2/2015 | Dalal ............... A61B 5/02433 600/323 |
| 2016/0073890 | A1 | 3/2016 | Khachaturian |
| 2016/0216245 | A1 | 7/2016 | Sutton |
| 2018/0008149 | A1* | 1/2018 | Pekander ............... G01K 7/427 |
| 2019/0014990 | A1 | 1/2019 | Franz et al. |
| 2019/0154509 | A1 | 5/2019 | Koch et al. |
| 2019/0313914 | A1 | 10/2019 | Kirenko et al. |
| 2019/0357857 | A1 | 11/2019 | Tanaka et al. |
| 2020/0105407 | A1 | 4/2020 | Soreefan et al. |
| 2021/0174917 | A1 | 6/2021 | Timme et al. |
| 2021/0174952 | A1* | 6/2021 | Leong .................... H04Q 9/00 |
| 2022/0130035 | A1 | 4/2022 | Addison et al. |

FOREIGN PATENT DOCUMENTS

| | | |
|---|---|---|
| JP | 5398784 B2 | 1/2014 |
| WO | 2014/012070 A1 | 1/2014 |
| WO | 2020146596 A1 | 7/2020 |

OTHER PUBLICATIONS

Invitation to Pay Additional Fees and, Where Applicable, Protest Fee from International Application No. PCT/US2021/071993, dated Feb. 7, 2022, 9 pp.

Lin et al., "A Thermal Camera based Continuous Body Temperature Measurement System," 2019 IEEE/CVF International Conference on Computer Vision Workshop (ICCVW), retrieved Jul. 17, 2020, retrieved from https://openaccess.thecvf.com/content_ICCVW_2019/papers/CVPM/Lin_A_Thermal_Camera_Based_Continuous_Body_Temperature_Measurement_System_ICCVW_2019_paper.pdf, 7 pp.

Notice of Allowance and Interview Summary from U.S. Appl. No. 17/080,506 dated Jan. 31, 2023, 13 pp.

* cited by examiner

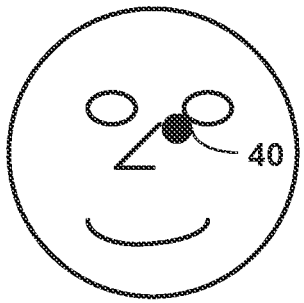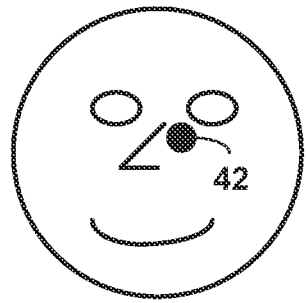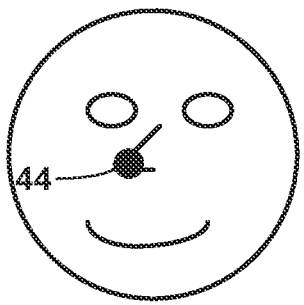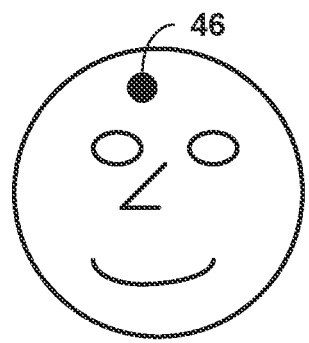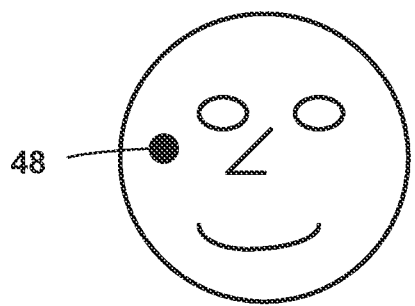
FIG. 5

TEMPERATURE MONITORING WITH A THERMAL CAMERA

CROSS-REFERENCE TO RELATED APPLICATION

This application is a divisional of U.S. patent application Ser. No. 17/080,506, filed Oct. 26, 2020, and entitled, "TEMPERATURE MONITORING WITH A THERMAL CAMERA," which is herein incorporated by reference in its entirety.

TECHNICAL FIELD

The disclosure relates generally to subject monitoring.

BACKGROUND

Thermal cameras are currently used for monitoring subjects in high density crowded environments, such as airports, waiting rooms, and so on. These cameras may operate in a spot check mode, measuring body temperature one subject at a time, at one point in time.

SUMMARY

In general, this disclosure is directed to devices, systems, and techniques for contactless monitoring of a temperature of a patient in a hospital or other clinical environment via a thermal camera. In some examples, the temperature of the patient can be continuously monitored using the devices, systems, and techniques described herein. For example, a thermal camera may be used to determine a measure of a core temperature of a patient. The devices, systems, and techniques of this disclosure may take into account movement of the patient relative to the thermal camera, environmental factors, such as ambient air temperature, and/or physiological factors of the patient when providing the measure of the core temperature of the patient.

In some examples, a system includes a thermal camera, a memory, and processing circuitry coupled to the thermal camera and the memory, the processing circuitry being configured to: acquire a core temperature of a patient; acquire, via the thermal camera, a first thermal image associated with the patient; determine, based on the first thermal image, a first sensed temperature of a location associated with the patient; determine a core temperature delta between the core temperature and the first sensed temperature; acquire, via the thermal camera, a second thermal image associated with a patient; determine, based on the second thermal image, a second sensed temperature of the location; determine, based on the second sensed temperature and the core temperature delta, a measure of the core temperature; and output the measure of the core temperature.

In some examples, a method includes acquiring, by processing circuitry, a core temperature of a patient; acquiring, by the processing circuitry, a first thermal image associated with the patient; determining, by the processing circuitry and based on the first thermal image, a first sensed temperature of a location associated with the patient; determining, by the processing circuitry, a core temperature delta between the core temperature and the first sensed temperature; acquiring, by the processing circuitry, a second thermal image associated with the patient; determining, by the processing circuitry and based on the second thermal image, a second sensed temperature of the location; determining, by processing circuitry and based on the second sensed temperature and the core temperature delta, a measure of the core temperature; and outputting the measure of the core temperature.

In some examples, a system is disclosed including a thermal camera, a depth camera, a memory, and processing circuitry coupled to the thermal camera and the memory, the processing circuitry being configured to: at a first time, via the depth camera, acquire a first distance between at least one of the depth camera or the thermal camera and a patient; control a first angle associated with a region of interest (ROI) of the thermal camera based on the first distance; acquire, via the thermal camera, a first thermal image associated with the patient; determine, based on the first thermal image, a first sensed temperature of a location associated with the patient; acquire, at a second time different than the first time, via the depth camera, a second distance between at least one of the depth camera or the thermal camera and the patient; control a second angle associated with the ROI of the thermal camera based on the second distance; acquire, via the thermal camera, a second thermal image associated with the patient; and determine, based on the second thermal image, a second sensed temperature of the location associated with the patient.

In some examples, a method includes acquiring, by processing circuitry at a first time via a depth camera, a first distance between at least one of the depth camera or a thermal camera and a patient; controlling, by the processing circuitry, a first angle associated with a region of interest (ROI) of the thermal camera based on the first distance; acquiring, by the processing circuitry via the thermal camera, a first thermal image associated with the patient; determining, by the processing circuitry and based on the first thermal image, a first sensed temperature of a location associated with the patient; acquiring, by the processing circuitry at a second time different than the first time, a second distance between at least one of the depth camera or the thermal camera and the patient; controlling, by the processing circuitry, a second angle associated with the ROI of the thermal camera based on the second distance; acquiring, by the processing circuitry via the thermal camera, a second thermal image associated with the patient; and determining, by the processing circuitry and based on the second thermal image, a second sensed temperature of the location.

This summary is intended to provide an overview of the subject matter described in this disclosure. This summary is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

FIG. 5 is a conceptual diagram illustrating example sensed temperatures at different locations on the face of a patient.

DETAILED DESCRIPTION

Example devices and systems described herein include a thermal camera configured to capture a thermal image of a location associated with a patient, e.g., on the patient or on an object (e.g., clothing, bed linens, a blanket, and the like) in direct or indirect contact with the patient. The location can be selected such that a temperature of the location changes as a function of a core temperature of the patient. Processing circuitry is configured to determine a measure of a core temperature of the patient based on the thermal image. With some patient conditions, such as conditions caused by the Covid-19 virus, technologies to automatically, continuously and robustly record patient temperature without physical contact, or even without going into the same room as the patient, may be useful in some settings, such as clinical settings. While the techniques of this disclosure are discussed primarily with reference to clinical settings, the techniques may be applied in other settings, such as nursing homes, schools, aircraft, cruise ships, airports, or any other area where people may be monitored.

Temperature may be an important indicator of certain possible patient conditions. For example, one of the symptoms of many viral, bacterial or other infections may be an elevated core temperature. As some patient conditions may be highly communicable, minimizing the amount of physical contact between clinicians and patients with such conditions (or who potentially have such conditions) may be useful. According to the devices, systems, and techniques of this disclosure, a measure of a core temperature of a patient may be monitored continuously without requiring frequent physical contact between a clinician and a patient. While a "patient" is generally referred to throughout the description, the patient may be any subject in any setting in which contactless temperature monitoring may be useful.

Figure 1:
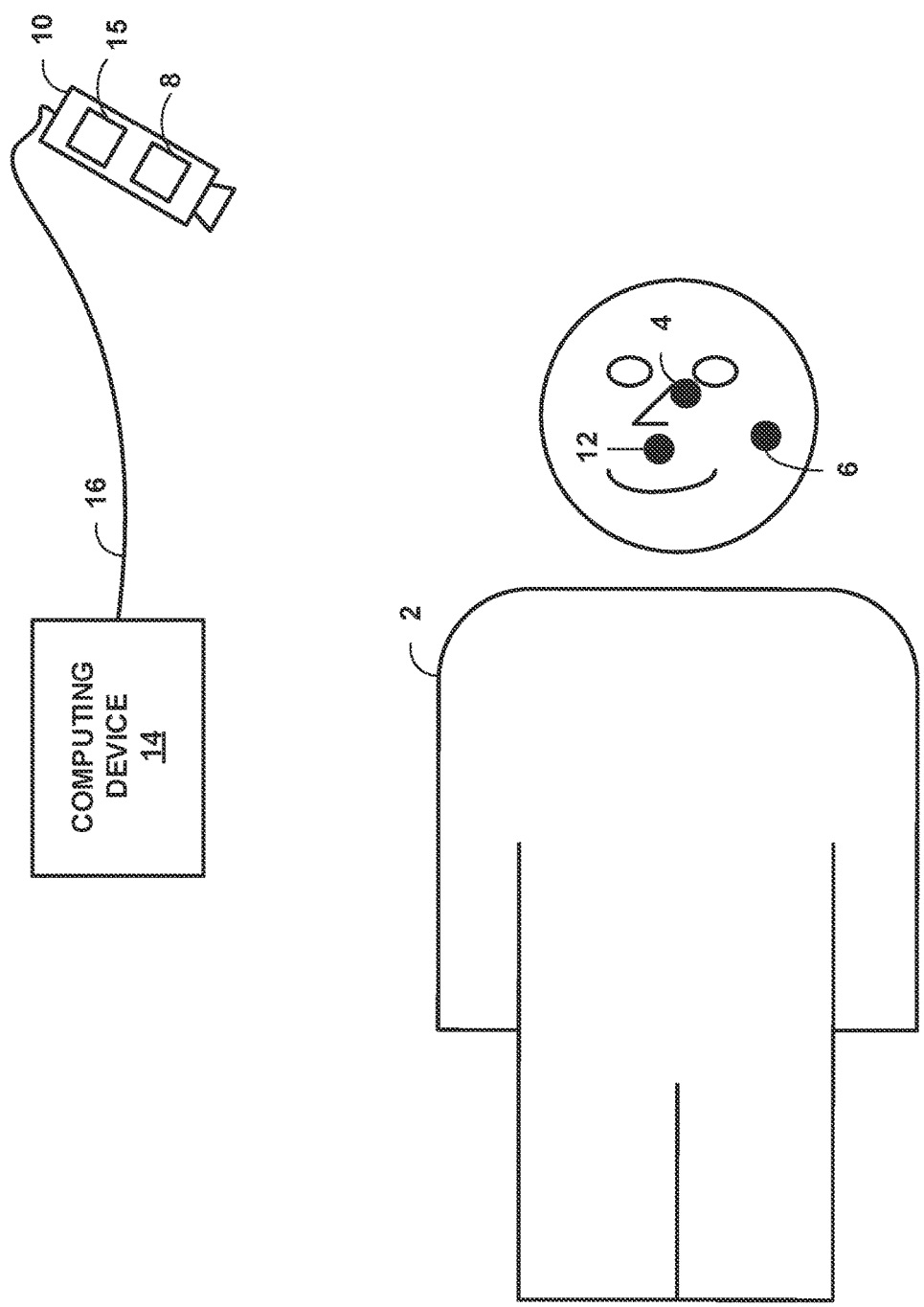
FIG. 1 is a conceptual diagram illustrating the monitoring of a temperature of a patient via a thermal camera.

FIG. 1 is a conceptual diagram illustrating the monitoring of a temperature of a patient via an example thermal camera. Thermal camera 10 is configured to monitor a temperature of patient 2 at a location associated with patient 2, e.g., on the patient 2 (e.g., on a skin surface, in a body cavity visible to thermal camera 10, or the like) or on an object (e.g., clothing, bed linens, a blanket, and the like) in direct or indirect contact with the patient. The location is selected such that a temperature of the location changes as a core temperature of patient 2 changes. As a result, a temperature at the location may be indicative of a core temperature of patient 2. A core temperature can refer to, for example, a temperature of one or more internal organs of patient 2, such as, but not limited to, the heart, liver, brain, or blood of patient 2.

For example, thermal camera 10 may monitor a temperature of patient 2 on the surface of the face of patient 2. In various examples, thermal camera 10 may sense the temperature of patient 2 near a tear duct at location 4, a cheek at location 6, under the nose at location 12, or at any other exposed skin location on patient 2, such as lips, forehead, and the like. As used herein a face may be any exposed skin on the head of patient 2. In some examples, the location may be any exposed skin of patient 2 (e.g., not just the face), such as exposed skin on an arm, a neck, a leg, a torso, a hand, and/or a foot, of patient 2. In some examples, a sensed temperature at a certain location, such as location 4, may correspond better to an actual core temperature of patient 2 than other locations associated with patient 2, such as a hand of patient 2.

In some examples, the location associated with patient 2 may be a point, such as may be represented by a single pixel of an image captured by thermal camera 10. In other examples, the location may be a region of interest, such as may be represented by a plurality of pixels of an image captured by thermal camera 10.

Thermal camera 10, which may also be referred to as a thermographic camera or a thermal imaging camera, can be configured to create an image using infrared radiation. Thermal camera 10 is communicatively coupled to computing device 14 through link 16. Link 16 may be a wired, wireless or optical connection. While the techniques of this disclosure are generally discussed with respect to computing device 14 and thermal camera 10, in some examples, the techniques of this disclosure may be performed by thermal camera 10 without computing device 14. In some example, thermal camera 10 may include a depth camera 8, and/or another camera 15, as will be discussed later in this disclosure.

By monitoring the temperature of location 4 via thermal camera 10, computing device 14 may determine a continuous measure of the patient's core temperature over time.

Figure 2:
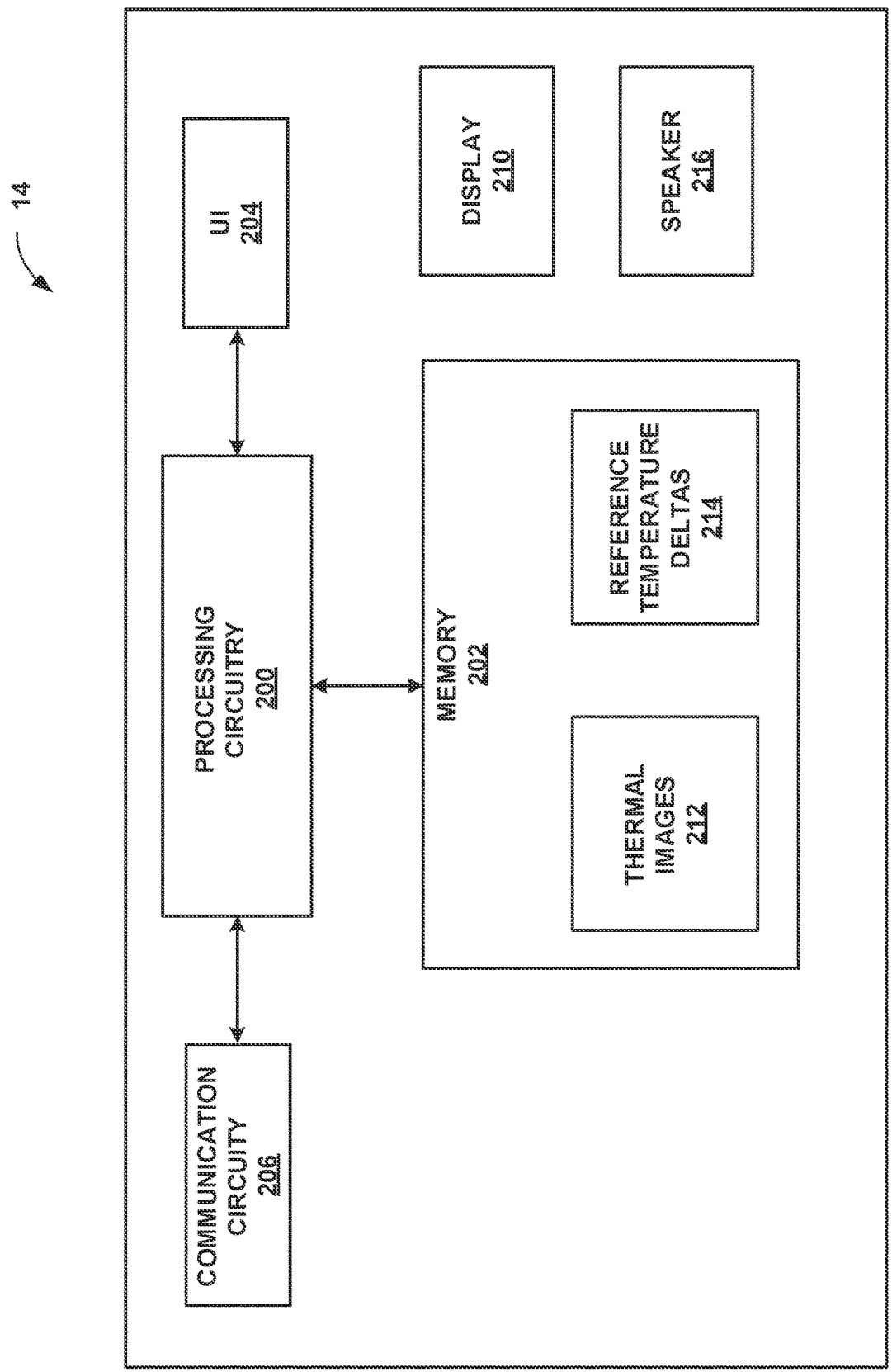
FIG. 2 is a block diagram illustrating an example computing device.

FIG. 2 is a functional block diagram illustrating an example configuration of a computing device 14 configured to perform the techniques of this disclosure. In the example of FIG. 2, computing device 14 includes processing circuitry 200, memory 202, user interface (UI) 204, communication circuitry 206, display 210, and speaker 216. In some examples, computing device 14 may be part of or include thermal camera 10 and/or depth camera 8. In some examples, computing device 14 may be a dedicated hardware device with dedicated software for the programming, controlling and/or receiving sensed temperatures from thermal camera 10. In some examples, computing device 14 may be a dedicated hardware device with dedicated software for the programming, controlling and/or receiving sensed depths from depth camera 8. Alternatively, computing device 14 may be a medical computing device that processes sensed data, such as vital statistics, for display via display 210 or audible presentation via speaker 216. In some examples, computing device 14 may be an off-the-shelf computing device, e.g., a laptop computer or smartphone running a mobile application that enables computing device 14 to program, control and/or receive sensed temperatures from thermal camera 10 and/or the sensed depths from depth camera 8.

Memory 202 is configured to store thermal images taken by thermal camera 10 in thermal images 212. Memory 202 is also configured to store reference temperature deltas in reference temperature deltas 214, which are described in further detail below. Example reference temperature deltas include, but are not limited to, a core temperature delta, a face temperature delta, a clothing temperature delta, a bedding temperature delta, or other temperature deltas.

In some examples, a user of computing device 14 may be a clinician, such as a physician, nurse or other healthcare worker. In some examples, display 210 is configured to, under the control of processing circuitry 200, display a measure of the core temperature of patient 2 determined by processing circuitry 200. In addition to or instead of displaying the measure of core temperature, in some examples, speaker 216, which may include any suitable noise generation circuitry, may output an audible representation of the measure of the core temperature of patient 2.

Processing circuitry 200 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, which may include one or more program modules, which are executable by processing circuitry 200. When executed by processing circuitry 200, such program instructions may cause processing circuitry 200 and computing device 14 to provide the functionality ascribed to them herein. The program instructions may be embodied in software, firmware and/or RAMware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, processing circuitry 200 of computing device 14 may be configured to provide some or all of the functionality ascribed to computing device 14, thermal camera 10, depth camera 8, and/or another camera 15.

Figure 3:
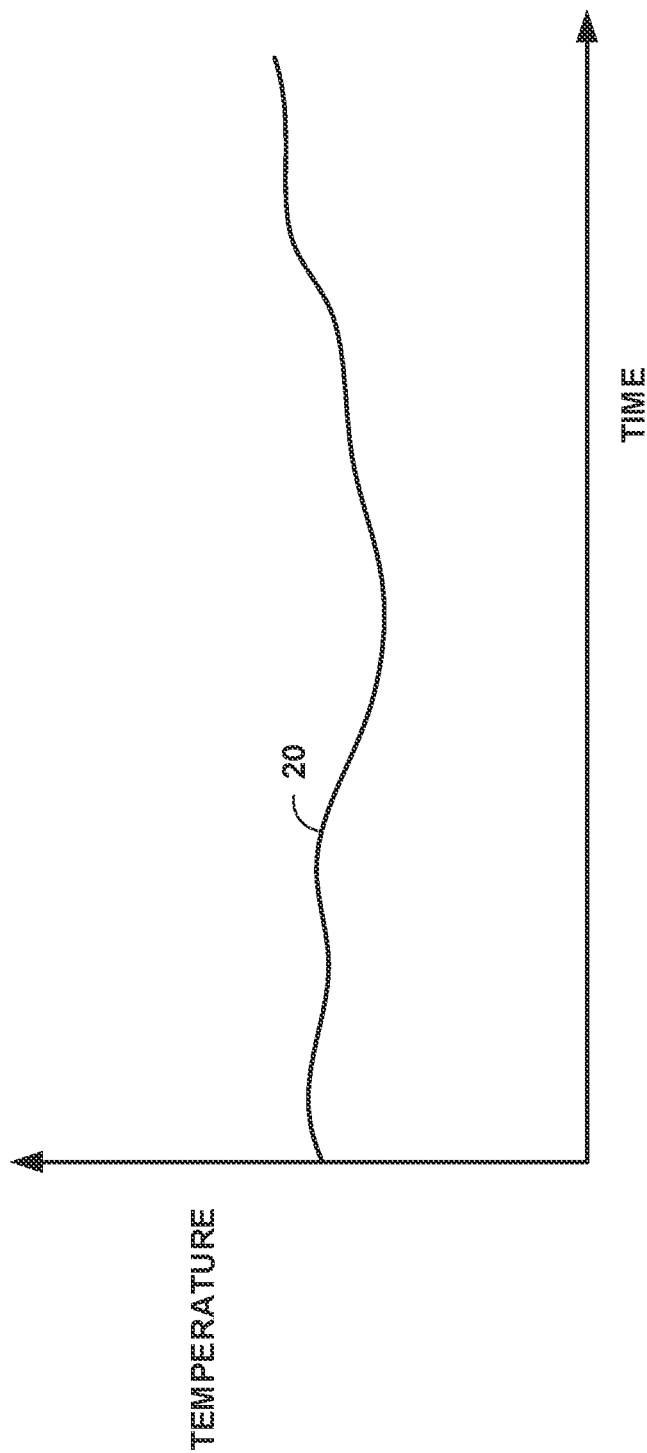
FIG. 3 is a graph illustrating an example of a continuous measure of a patient's temperature.

FIG. 3 is a graph illustrating an example of a continuous measure of a patient's temperature. In the example of FIG. 3, line 20 represents a sensed temperature of patient 2 at a location associated with patient 2 and determined by processing circuitry 200 of computing device 14, based on images captured by thermal camera 10 of FIG. 1. As can be seen, in this example, the temperature is continuously sensed over time, such as during a hospital stay by patient 2.

In some examples, thermal camera 10 may sense a temperature of patient 2 that may be different than a core temperature of patient 2. For example, thermal camera 10 may sense a temperature at location 4 (or other locations, such as location 6 or location 12) associated with patient 2 that may be higher or lower than the actual core temperature of patient 2. The difference in temperature as sensed at location 4 and the core temperature of patient 2 may be referred to as a core temperature delta. In some examples, thermal camera 10 may sense a temperature at, for example, location 4, while or within a relatively short time period (e.g., less than 200 seconds) of an actual core temperature sensing of patient 2. Processing circuitry 200 of computing device 14 may calibrate the sensed temperature from thermal camera 10 using the core temperature delta.

Processing circuitry 200 can determine the core temperature of patient 2 using any suitable technique, e.g., receive the core temperature of patient 2 from a clinician or patient monitoring equipment. For example, a clinician along or with the aid of patient monitoring equipment may measure a core temperature of patient 2 using any suitable technique, such as, but not limited to, using a thermometer introduced into a rectum, ear, armpit, or mouth of a patient or an implantable temperature sensor. The measurement of core temperature may be referred to as an actual core temperature. In some examples, this core temperature may be taken, for example, during intermittent spot checks carried out in the hospital by a clinician, or in other examples, only when patient 2 is first put into a hospital bed or admitted to the hospital. The clinician may manually input the actual core temperature into computing device 14 via UI 204 (FIG. 2), or processing circuitry 200 may automatically receive the actual core temperature from patient monitoring equipment. In either example, processing circuitry 200 may store the core temperature in memory 202 for use in continuous temperature monitoring of patient 2. For example, processing circuitry 200 may calibrate the temperature at, for example, location 4 using the known differences between the sensed thermal camera temperature at that point and the known core temperature, which can be, for example, the last measure of core temperature of patient 2 stored by memory 202.

Figure 4:
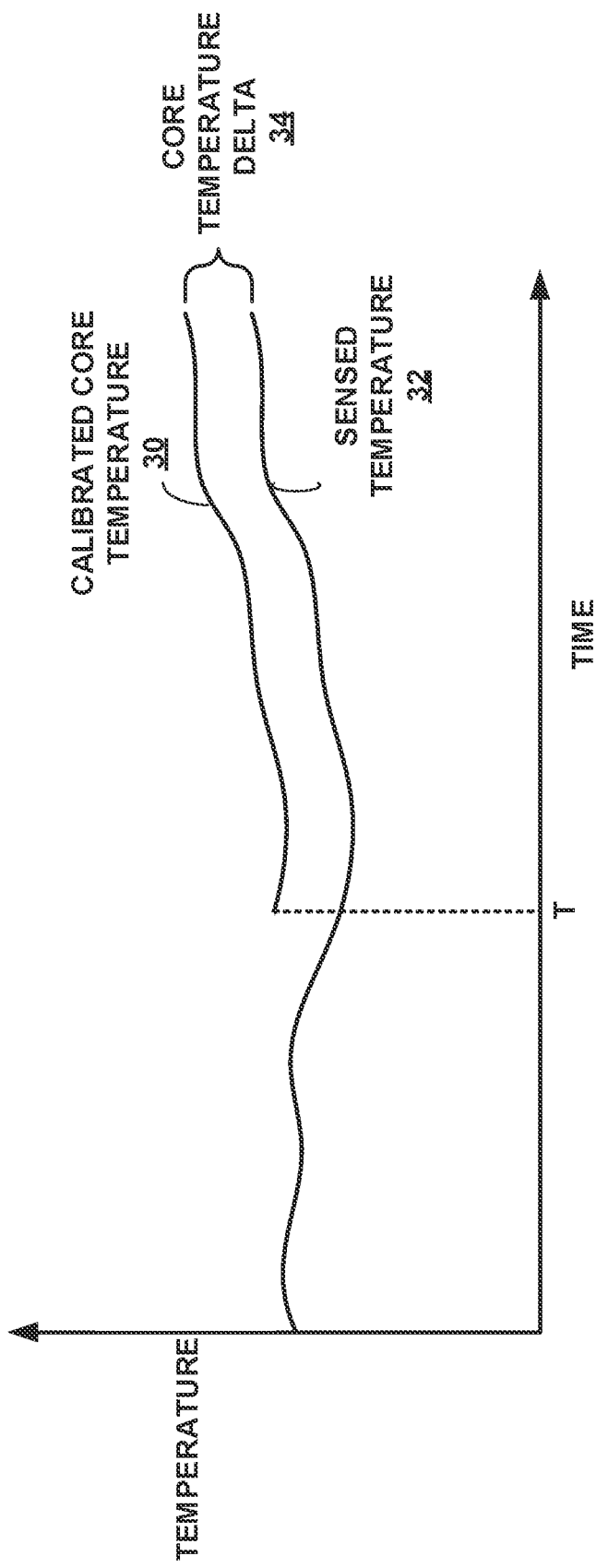
FIG. 4 is a graph illustrating example calibration techniques of this disclosure.

FIG. 4 is a graph illustrating example calibration techniques. A core temperature of patient 2 is determined at time T and processing circuitry 200 receives and stores the actual core temperature. Processing circuitry 200 also determines a sensed temperature of patient 2 at location 4 from a thermal image taken by thermal camera 10, which is shown as sensed temperature 32. In this example, the actual core temperature of patient 2 is higher than the sensed temperature determined based on the thermal image from thermal camera 10, the difference being a core temperature delta 34. Processing circuitry 200 determines and stores core temperature delta 34 in reference temperature deltas 214 (FIG. 2). In some example, the relationship between the actual core temperature of patient 2 and the sensed temperature of patient 2 at location 4 may be linear. In other examples, the relationship between the actual core temperature of patient 2 and the sensed temperature of patient 2 at location 4 may be non-linear. For example, the relationship between the actual core temperature of patient 2 and the sensed temperature of patient 2 at location 4 may vary based on the actual core temperature of patient 2 or the sensed temperature of patient 2 at location 4. After determining core temperature delta 34 and during subsequent temperature monitoring of patient 2 using thermal camera 10, processing circuitry 200 calibrates the sensed temperatures by at least adding the core temperature delta 34 to sensed temperature 32 to determine a measure of a core temperature, such as calibrated core temperature 30. Thus, the measure of the core temperature is an indication of the core temperature that is determined without actually measuring the core temperature of patient 2 using a technique requiring direct physical contact with patient 2, e.g., a thermometer introduced into a rectum, ear, armpit, or mouth of patient 2 technique. For example, by using a known difference, such as core temperature delta 34, between a sensed temperature of patient 2 at location 4 (or another location associated with patient 2) and an actual core temperature at a given point in time, a measure of the core temperature may be determined at a later point in time based on the sensed temperature of the patient at the later point in time and the known difference, where the sensed temperature is determined based on one or more thermal images from thermal camera 10 and without physically placing the temperature sensing device in contact with patient 2.

In some examples, computing device 14 may output a representation of calibrated core temperature 30 or an alert relating to calibrated core temperature 30 to a clinician, for example, through display 210, speaker 216, UI 204, or communication circuitry 206, such as to provide a visual, auditory and/or haptic representation of or alert regarding calibrated core temperature 30. In some examples, the representation of calibrated core temperature 30 that is outputted may be a numerical value of the core temperature of patient 2, words or words indicative of the temperature (e.g., low, normal, and/or elevated, relative to a predetermined temperature threshold), a color that changes as a function of the temperature (e.g., shades of red indicating temperatures greater than or equal to a threshold (e.g., 101 degree Fahrenheit) and shades of green representing temperatures less than the threshold), or any other suitable display that may convey the measure of core temperature to a user. In some examples, computing device 14 may output a representation of both calibrated core temperature 30 and sensed temperature 32 to a clinician.

In some examples, the actual core temperature of patient 2 may be lower than sensed temperature 32 determined using thermal camera 10. In such cases, processing circuitry 200 may subtract the core temperature delta 34 from the sensed temperature or add a negative core temperature delta to the sensed temperature in order to determine the measure of core temperature from sensed temperature 32. Processing circuitry 200 may continually add (or subtract) core temperature delta 34 to sensed temperature 32 to provide a measure of core temperature of patient 2. If a clinician or a device takes another spot check of the actual core temperature of patient 2 and provides the actual core temperature to processing circuitry 200 (e.g., via UI 204), processing circuitry 200 of computing device 14 may update the core temperature delta 34 and use the updated core temperature delta 34 to determine subsequent measures of the core temperature of patient 2. For example, processing circuitry 200 of computing device 14 may replace core temperature delta 34 with the updated core temperature delta in memory 202. In another example, processing circuitry 200 of computing device 14 may determine a mean, median, or mode of the updated core temperature delta and past core temperature deltas and use the mean, median, or mode of the core temperature deltas to determine the measure of the core temperature of patient 2.

In some examples, thermal camera 10 may be pointed at patient 2 and thermal camera 10 or computing device 14 may determine a map of sensed temperatures across the face of patient 2 and/or other region of patient 2 (e.g., one or more limbs) based on a thermal image from thermal camera 10. This map may be referred to as a face temperature map in examples in which the region of patient 2 being mapped includes the face, or more generally a temperature map in other examples. In some examples, thermal camera 10 or computing device 14 may determine a map of all the differences between the face (or sensed) temperature map to the actual core temperature to produce a map of core temperature deltas ("core temperature delta map"). Processing circuitry 200 may store the core temperature delta map in memory 202 and determine, using the core temperature delta map, a measure of the core temperature of patient 2 based on a thermal image of any part of the face (or other part) of patient 2 and a core temperature delta between that part of the face (or other patient part) of patient 2 and the actual core temperature of patient 2.

The temperatures across the face of patient 2 may not be constant, but may vary with location. FIG. 5 is a conceptual diagram illustrating example sensed temperatures at different locations on the face of patient 2. For example, thermal camera 10 may sense a temperature at location 40 near a tear duct of patient 2 as 35.2° C. (95.4° F.). Thermal camera 10 may sense a temperature at location 42, also near a tear duct of patient 2, as 34.6° C. (94.3° F.). Thermal camera 10 may sense a temperature at location 44, on the nose of patient 2, as 30.6° C. (87.1° F.). Thermal camera 10 may sense a temperature at location 46, on the forehead of patient 2, as 33.9° C. (93.0° F.). Thermal camera 10 may sense a temperature at location 48, on the cheek of patient 2, as 33.2° C. (91.8° F.). Thus, the sensed temperatures may vary based on the location at which thermal camera 10 senses the temperature of patient 2. For example, the difference between the sensed temperature at location 40 and location 42 may be 0.6° C. (1.1° F.). The difference between the sensed temperature at location 40 and location 44 may be 4.6° C. (8.3° F.). The difference between the sensed temperature at location 40 and location 48 may be almost 2° C. (3.6° F.).

Figure 6:
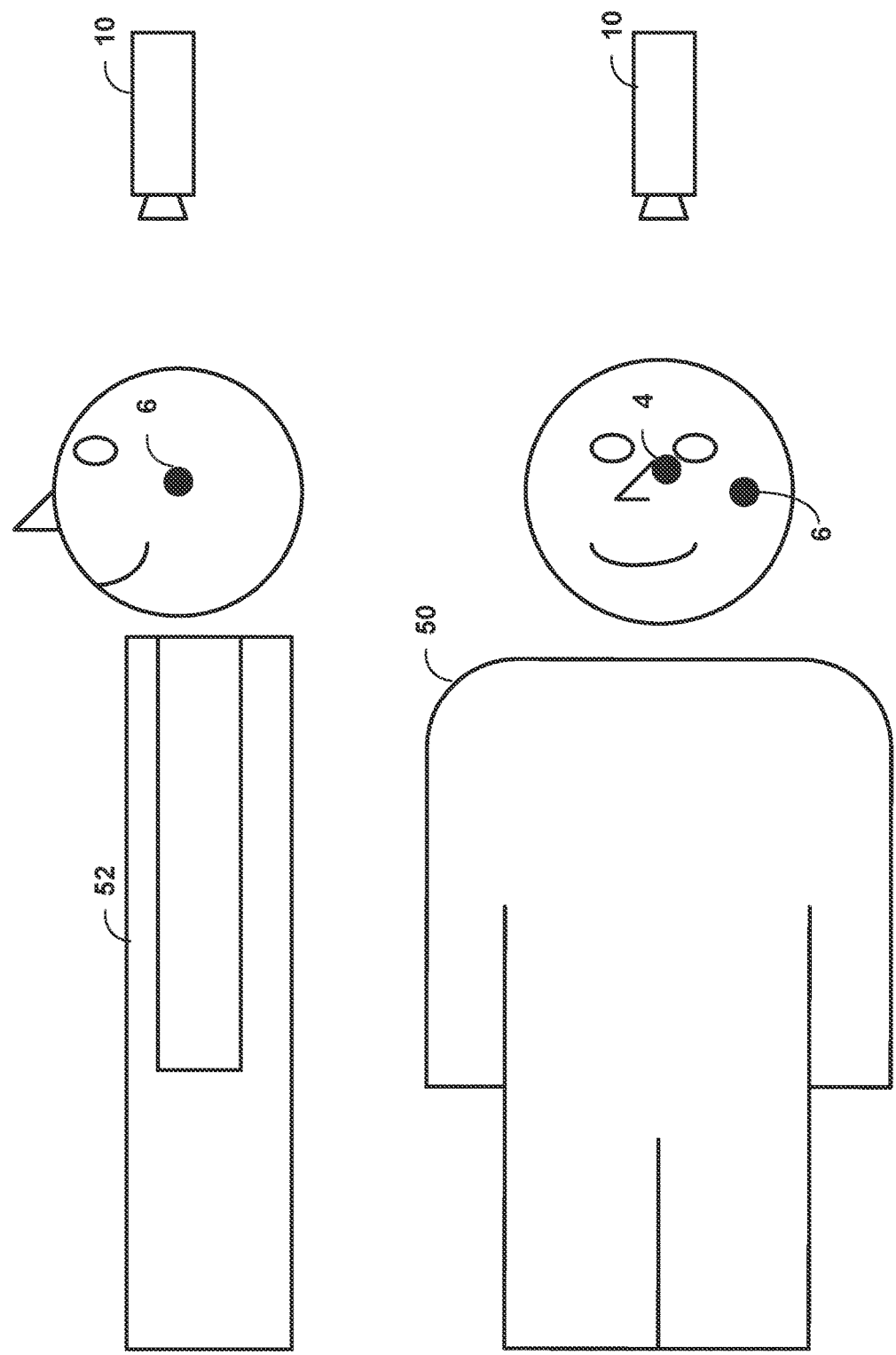
FIG. 6 is a conceptual diagram illustrating example locations for sensing a temperature of a patient.

Thermal camera 10 may be in a fixed position in some examples or automatically or manually movable within a particular range of locations in a particular setting (e.g., a hospital room). In some circumstances, depending on patient position, a location, such as location 4, may be obscured from the view of thermal camera 10, and, therefore, may be only partially visible or not visible at all in a thermal image taken by thermal camera 10. For example, as shown in FIG. 6, patient 2 may move from position 50 (e.g., a supine position) to position 52 such that they are lying on their side. While location 4 may be in the line of sight of thermal camera 10 when patient 2 is in position 50, location 4 may not be visible to thermal camera 10 when patient 2 is in position 52. However, other parts of the face of patient 2 may still be within the line of sight of thermal camera 10 when patient 2 is in position 52. For example, location 6 may still be in the line of sight of thermal camera 10.

Computing device 14 may store information indicative of the relationship between the sensed temperature at location 4 and at location 6 based, for example, on the thermal mapping of the face of patient 2. As such, processing circuitry 200 of computing device 14 may determine a measure of a core temperature of patient 2 based on an image from thermal camera 10 even after patient 2 moves from position 50 to position 52 (or between other two positions that result in a particular sensed location becoming partially or fully obscured from view of thermal camera 10). By enabling processing circuitry 200 to determine a measure of core temperature even after patient 2 moves, the techniques of this disclosure facilitate continuous and contactless monitoring of a measure of the core temperature of patient 2. In this manner, a clinician or device may not need to recheck the core temperature of patient 2 and processing circuitry 200 may not need to determine a new face temperature delta just because the patient moved so that location 4 is no longer in the line of sight of thermal camera 10. For example, processing circuitry 200 of computing device 14 may determine a map of the temperatures across the face of patient 2 at a particular time, such that the environmental conditions are the same or nearly the same, and at a plurality of locations on face 2 (e.g., at two or more discrete points, such as the tip of the nose, the tear ducts, the tip of the chin, etc., or regions, such as the whole face, the cheeks, the forehead, the nose, and the like, or at two or more regions of interest), and find the relationship between each location of the plurality. The differences in temperature between two locations on the face of patient 2 may be referred to as a face temperature delta. In some examples, processing circuitry 200 may determine, e.g., based on information stored by memory 202, that location 4 is 2° C. warmer than location 6. Therefore, when patient 2 moves from position 50 to position 52 and thermal camera 10 is now sensing a temperature at location 6, processing circuitry 200 may add this face temperature delta of 2° C. to the sensed temperature at location 6 to determine a measure of the temperature at location 4.

While discussed primarily herein as a map of temperatures across the face of patient 2, in some examples, rather than a map of temperatures across the face of patient 2, processing circuitry 200 may determine a map of temperatures of any of a plurality of locations associated with the patient. For example, processing circuitry 200 may determine a map of temperatures across any exposed skin of patient in the line of sight of thermal camera 10 (e.g., hand, arm, neck and/or face). In another example, processing circuitry 200 may determine a map of temperatures across clothing, blanket, bed linens, and/or exposed skin of patient 2.

For example, processing circuitry 200 may determine, in response to patient 2 moving and based on a stored temperature map of the face of patient 2, a face temperature delta between a location 4 on the face of patient 2 and location 6 on the face of patient 2. For example, processing circuitry 200 may analyze images from thermal camera 10, depth camera 8, and/or another camera 15 to determine whether patient 2 has moved. In some examples, processing circuitry may use image analysis to determine features of the face of patient 2 and may determine the patient has moved based on the feature of the face of patient 2 moving in one image when compared to a previous image. Processing circuitry 200 may also determine, based on the face temperature delta and a sensed temperature at location 6, a measure of a temperature at location 4. In some examples, processing circuitry 200 of computing device 14 may determine, based on the measure of the core temperature at location 6 on the face of patient 2 and the core temperature delta, a measure of the core temperature and output the measure of the core temperature, such as to a display, a speaker, and/or a nurses' station.

Figure 7:
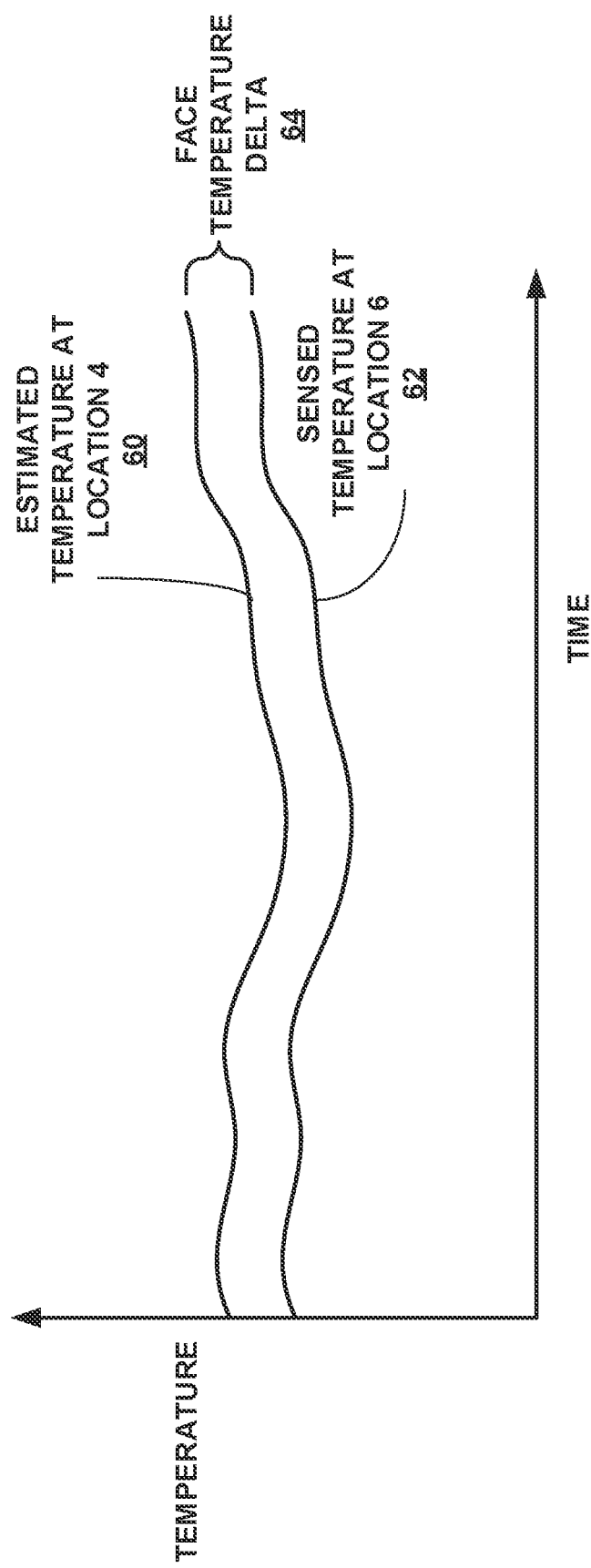
FIG. 7 is a graph diagram illustrating adding of a temperature delta to a sensed temperature according to example techniques of this disclosure.

FIG. 7 is a graph diagram illustrating the adding of a face temperature delta to a sensed temperature to determine a measure of core temperature according to example techniques of this disclosure. In the example of FIG. 7, processing circuitry 200 determines sensed temperature at location 6 from a thermal image of thermal camera 10 and may add the face temperature delta 64 to (or subtract the face temperature delta 64 from) the sensed temperature at location 6 to estimate the temperature of patient 2 at location 4.

In some examples, rather than estimate the temperature of patient 2 at location 4, processing circuitry 200 may calibrate the sensed temperature at location 6 with the core temperature as discussed above with respect to FIG. 4. In some examples, processing circuitry 200 or thermal camera 10 may determine a map of all differences from the sensed face temperature to the actual core temperature. In such examples, processing circuitry 200 or thermal camera 10 may calibrate any point on the face of patient 2 so as to determine a measurement of a core temperature of patient 2.

In some examples, processing circuitry 200 of computing device 14 may determine a mean, median, or mode of the sensed temperatures across the face of patient 2 at a given time from a given thermal image. Processing circuitry 200 may determine a difference between the actual core temperature and the mean, median, or mode of the sensed temperatures to calibrate the core temperature determined based on a thermal image. In some examples, computing device 14 may remove outlying sensed temperatures from the determination of the mean, median, or mode. For example, processing circuitry 200 may remove sensed temperatures that are outside of a predetermined range, such as the range on the order of between the $5^{th}$-$35^{th}$ to the $65^{th}$-$95^{th}$ percentile (e.g., the $25^{th}$ to $75^{th}$ percentile) of sensed temperatures. By removing outlying sensed temperatures, the resulting measure of the core temperature of patient 2 may be more stable.

Figure 8:
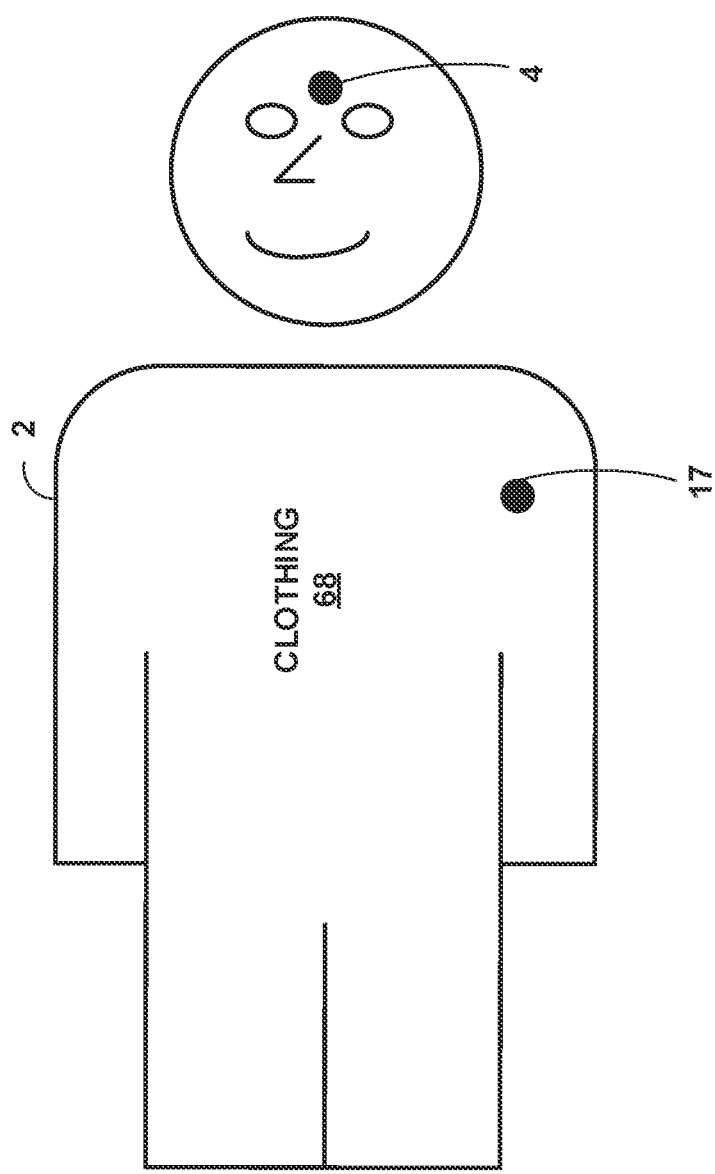
FIG. 8 is a conceptual diagram illustrating example thermal camera techniques.

While determination of a sensed temperature of a location on a face of patient 2 is primarily referred to in the description of FIGS. 3-7, in other examples, the location associated with the patient can be somewhere other than the face. For example, as shown in FIG. 8, in some examples, thermal camera 10 may sense a temperature of patient 2 at a location, such as location 17, that may be on the clothing 68 contacting patient 2. Similarly, to the examples of FIG. 4 and FIG. 7, processing circuitry 200 or thermal camera 10 may determine a map of sensed temperatures on clothing 68 contacting patient 2 or a map of sensed temperatures on clothing 68 contacting patient 2 and the face of patient 2. Processing circuitry 200 may determine a clothing temperature delta between location 17 other locations, such as location 4, or may determine a temperature delta between location 17 and the measured core temperature of patient 2. Processing circuitry 200 of computing device 14 may apply any of the techniques disclosed herein to either determine a measure of core temperature of patient 2 based on the clothing temperature delta and a sensed temperature at location 17 (from thermal camera 10), or to approximate a temperature at another location, such as location 4.

Figure 9:
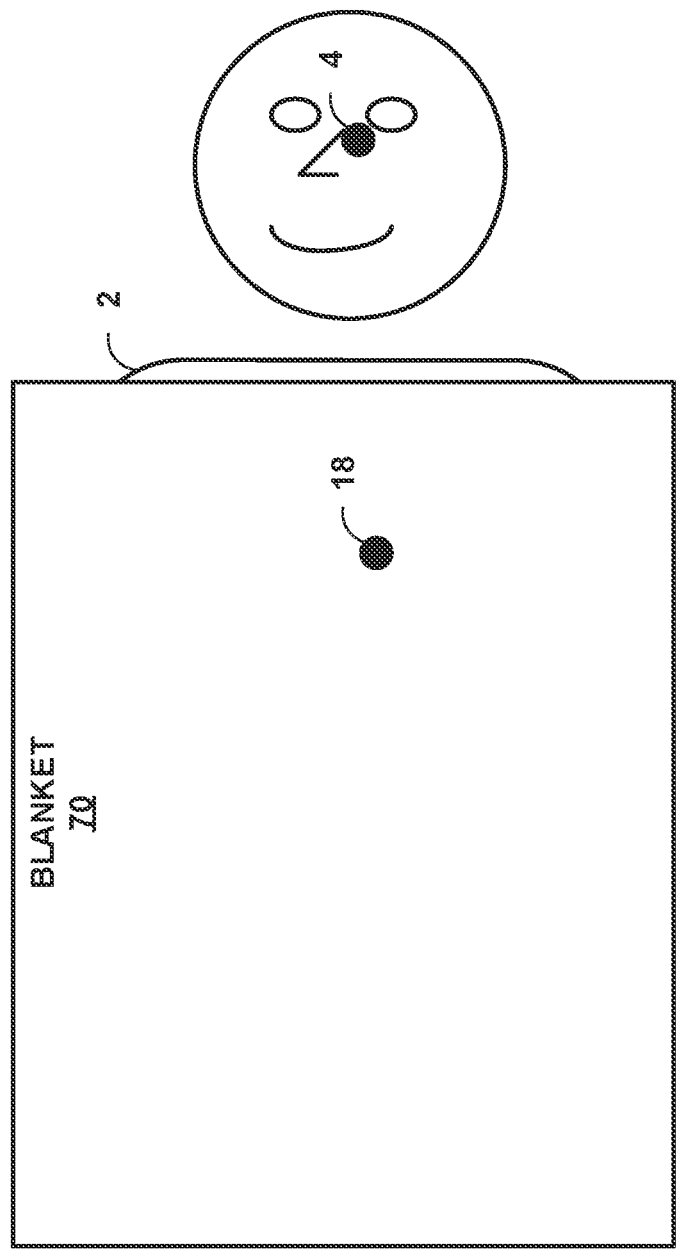
FIG. 9 is a conceptual diagram illustrating further example thermal camera techniques.

As another example, as shown in FIG. 9, rather than sense a temperature at a location on clothing 68 contacting patient 2, thermal camera 10 may sense a temperature at location 18 on blanket 70 contacting patient 2 or other bed linens directly or indirectly contacting patient 2. Similarly, to the examples of FIG. 4, FIG. 7, and FIG. 8, processing circuitry 200 or thermal camera 10 may determine a map of sensed temperatures on blanket 70 (or other bed linens) contacting patient 2 or a map of sensed temperatures on blanket 70 (or other bed linens) and the face of patient 2. Processing circuitry 200 may determine a bedding temperature delta between the temperatures determined based on a thermal image captured by thermal camera 10 at location 18 other locations, such as location 4, or may determine a temperature delta between location 18 and the actual core temperature of patient 2. Processing circuitry 200 of computing device 14 may apply any of the techniques disclosed herein to either determine a measure of core temperature of patient 2, or to approximate a temperature at another location, such as location 4.

In some examples, thermal camera 10 may include a depth camera 8 (FIG. 1), computing device 14 may include a depth camera or a separate depth camera may be used with thermal camera 10 and/or computing device 14. In some examples, processing circuitry 200 of computing device 14 may change the angle associated with a region of interest (ROI) based on a depth sensed by depth camera 8. Referring back to FIG. 1, as discussed above, thermal camera 10 may capture thermal images of patient 2, from which processing circuitry 200 can determine a temperature at a location associated with patient 2. This sensed temperature may be indicative of the core temperature of patient 2. In some examples, the location may be a point or a region of interest ROI which covers a larger area than a point.

Figure 10:
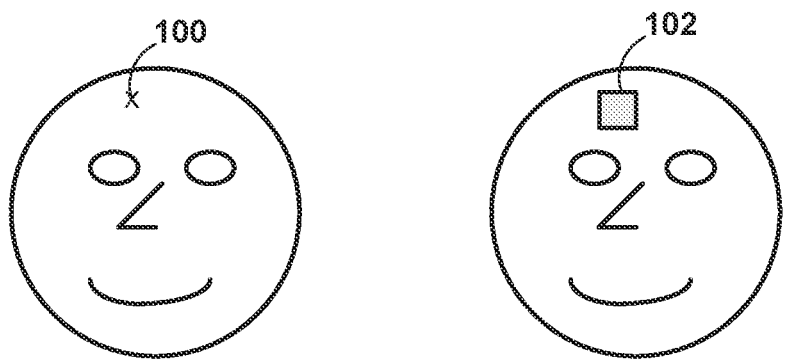
FIG. 10 is a conceptual diagram illustrating an example of monitoring a temperature in a region of interest of a patient.

FIG. 10 is a conceptual diagram illustrating an example of monitoring a temperature in a ROI 102 of patient 2. In some examples, thermal camera 10 may monitor a point location, such as point 100 marked by the "x" in FIG. 10. A point may be represented by a single pixel of a thermal image captured by thermal camera 10. In other examples, thermal camera 10 may monitor an ROI 102. ROI 102 is not a point, but rather an area, such as is shown in the square in FIG. 10. Thus, ROI 102 may be represented by a plurality of pixels in a thermal image captured by thermal camera 10. Each pixel can have the same size in some examples, and can be different sizes in other examples. Processing circuitry 200 of computing device 14 may determine a mean, median, or mode of sensed temperatures within ROI 102 in the thermal image, such that the mean, median, or mode of sensed temperatures is a mean, median, or mode of the temperatures at two or more pixels (a subset of pixels or all the pixels) within ROI 102 at the particular time the thermal image was taken.

In some examples, processing circuitry 200 may remove outlying sensed temperatures within ROI 102 from the determination of the mean, median, or mode. For example, processing circuitry 200 may remove sensed temperatures that are outside of a predetermined range, such as the range on the order of between the $5^{th}$-$35^{th}$ to the $65^{th}$-$95^{th}$ percentile (e.g., the $25^{th}$ to $75^{th}$ percentile) of sensed temperatures before determining the mean, median, or mode. The determined mean, median, or mode temperature of an ROI, such as ROI 102, may be referred to herein as the ROI temperature or sensed temperature. By using an ROI temperature rather than a point temperature, the sensed temperature may be more stable (e.g., have less variation) over time. The ROI may be a certain size given a particular distance. In some examples, the ROI may be predefined by a manufacturer of computing device 14 and/or thermal camera 10, or selected by a user, such as a clinician. For example, a clinician may define the ROI by interacting with UI 204 to click a point or outline an ROI on an image of patient 2 or in a graphic representing a patient or portion of a patient. As another example, a clinician may select an ROI size and location by selecting from a plurality of predetermined ROIs made available for selection via computing device 14. In some examples, the ROI may be an area of patient 2 that may correspond well to the actual core temperature of patient 2, such as a forehead of patient 2.

Figure 11A:
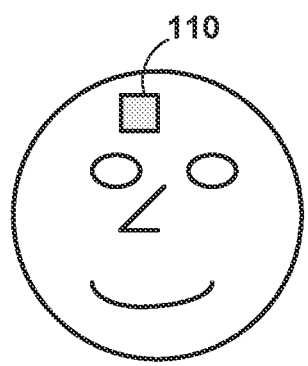
FIGS. 11A-11C are conceptual diagrams illustrating region of interest (ROI) temperature sensing without adjusting the angle associated with the ROI based on distance.
Figure 11B:
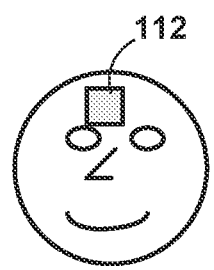
Figure 11C:
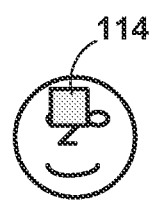

FIGS. 11A-11C are conceptual diagrams illustrating ROI temperature sensing without adjusting the angle associated with the ROI based on distance. In the example of FIG. 11A, ROI 110 of patient 2 is of a same size as ROI 102 of FIG. 10. Without adjusting the angle associated with the ROI, such as based on a depth sensed by depth camera 8, when patient 2 moves further from thermal camera 10, the ROI effectively grows relative to the face of the subject if the angle associated with the ROI does not change. This relative change in the effective ROI may be referred to herein as a changing ROI. For example, in FIG. 11B, ROI 112 (when patient 2 is further from thermal camera 10 than in FIG. 11A) covers a larger area of the forehead of patient 2 than in FIG. 11A. When patient 2 moves even further away from thermal camera 10, the ROI effectively grows again, as shown in FIG. 11C. For example, ROI 114 covers most of the forehead, most of an eye and part of the bridge of the nose of patient 2.

As discussed above, different locations of the face of patient 2 may have very different sensed temperatures. Therefore, if the ROI effectively changes in size when patient 2 moves towards or away from thermal camera 10, the sensed temperatures (from the thermal images captured by thermal camera 10) may vary. For example, the mean, median, or mode of ROI 110 of FIG. 11A may differ greatly than the mean, median, or mode of ROI 114 of FIG. 11C even if the core temperature of patient 2 has not changed. For example, the temperature difference between the nose and the forehead may differ significantly (by up to or above 5-10° C.). In order to help minimize the changes in the size of a ROI depending on the proximity of patient 2 to thermal camera 10, in some examples, the angle associated with the the ROI changes based on the distance between thermal camera 10 (or depth camera 8) and patient 2.

Figure 12A:
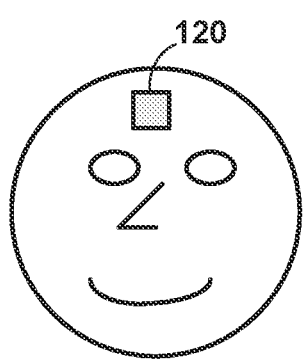
FIGS. 12A-12C are conceptual diagrams illustrating ROI temperature sensing with the use of a depth camera.
Figure 12B:
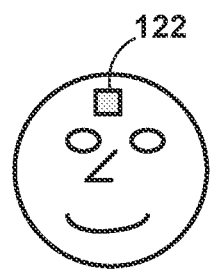
Figure 12C:
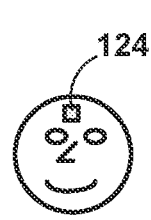

FIGS. 12A-12C are conceptual diagrams illustrating ROI temperature sensing with the use of a depth camera 8. For example, in FIG. 12A, ROI 120 covers or substantially covers the area or the same size area of the patient as ROI 122 of FIG. 12B, and ROI 124 of FIG. 12C even though the patient is at different distances from thermal camera 10. This unchanged effective ROI may be referred to herein as a fixed ROI. Such an arrangement may result in more stable ROI temperature and a more accurate determined measure of the core temperature of patient 2.

Figure 13:
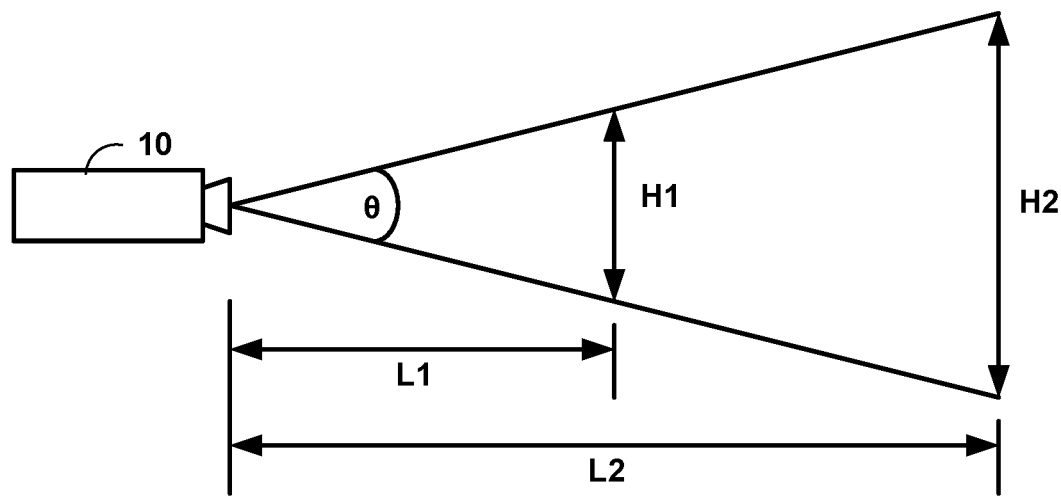
FIG. 13 is a conceptual diagram illustrating an example relationship between an ROI and distance from a thermal camera.

FIG. 13 is a conceptual diagram illustrating an example relationship between an ROI and distance from a thermal camera. At distance L1 from thermal camera 10, the ROI may have a height of H1. However, at distance L2 from thermal camera 10, the ROI may have a height of H2, which is greater than H1. However, for a given field of view angle θ, thermal camera 10 may use the same number of pixels to denote the height of objects H1 and H2.

Figure 14:
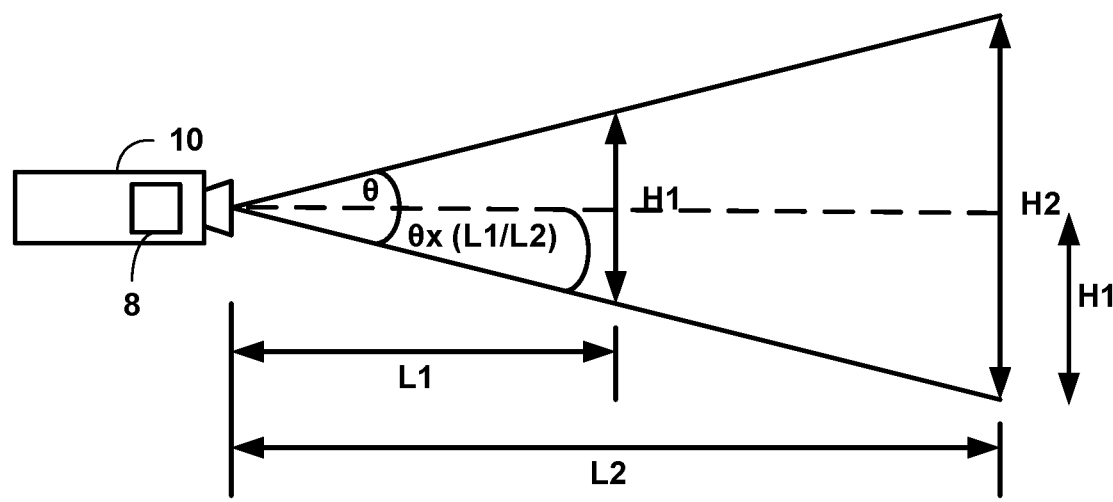
FIG. 14 is a conceptual diagram illustrating another example relationship between an ROI and distance from a thermal camera.

If thermal camera 10 were to use the same height (e.g. H1 at both distance L1 and distance L2 to keep the size of the ROI the same, then thermal camera 10 may use a smaller angle than θ and a smaller number of pixels at distance L2 than at distance L1. FIG. 14 is a conceptual diagram illustrating another example relationship between an ROI and distance from a thermal camera. In the example of FIG. 14, to sense an ROI temperature of an ROI at location L2 equal in size to the ROI at location L1, the number of pixels thermal camera 10 may be required to use may be less than at location L1. For example, the number of pixels that may be required may scale as L1/L2 in any one dimension (e.g., height or breadth of the ROI in the image). Therefore, in some examples, processing circuitry 200 may control thermal camera 10 to actually change the angle associated with the ROI to a different angle than θ, such as θ×(L1/L2) so as to keep the field of view focused on the same ROI on patient 2 such that the size of the ROI on patient 2 does not change (or does not significantly change) as patient 2 moves towards or away from thermal camera 10. For example, depth camera 8 may sense a distance L1 to patient 2 and computing device 14 or thermal camera 10 may use the distance L1 sensed by depth camera 8 to determine the angle associated with the ROI. When patient 2 moves away from thermal camera 10, depth camera 8 may determine a new distance L2 and processing circuitry 200 may determine a new angle associated with the ROI to be θ×(L1/L2) and control thermal camera 10 to change the angle associated with the ROI.

Figure 15:
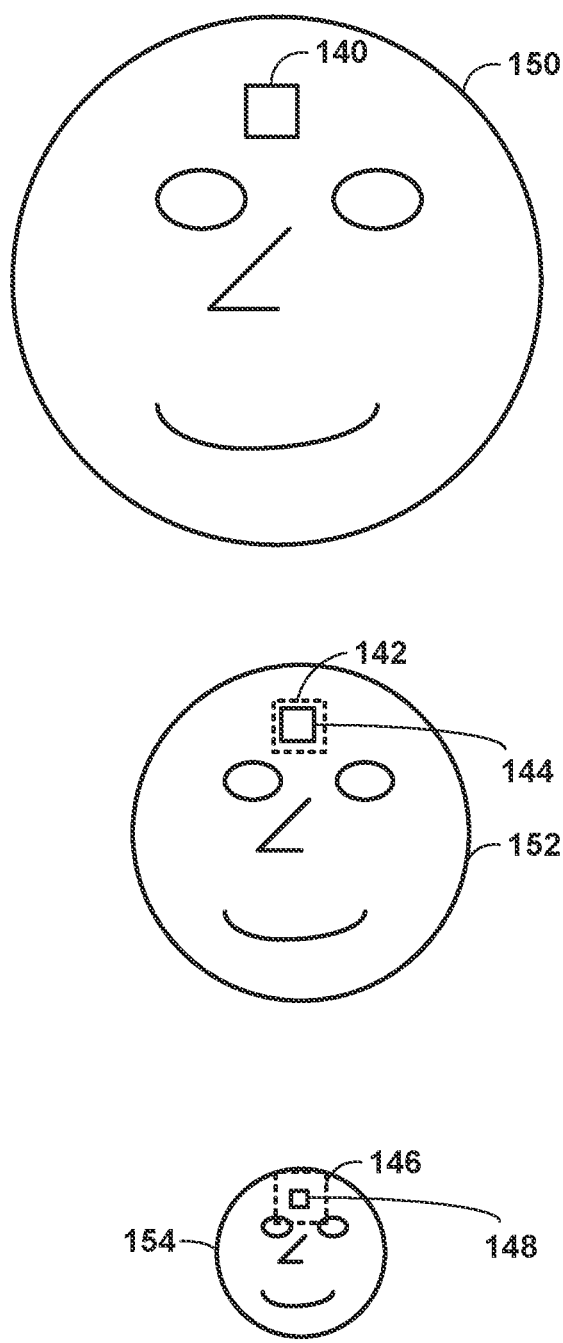
FIG. 15 is a conceptual diagram illustrating example differences between changing the angle associated with the ROI and not changing the angle associated with the ROI according to the techniques of this disclosure.

FIG. 15 is a conceptual diagram illustrating example differences between changing the angle associated with the ROI and not changing the angle associated with the ROI. When patient 2 is positioned near thermal camera 10 at location 150, ROI 140 may be the same for both a changed angle associated with the ROI based on the distance from thermal camera 10 (or depth camera 8) and a not changed angle associated with the ROI based on the distance between patient 2 and thermal camera 10 (or depth camera 8). When patient 2 moves to location 152 further away from thermal camera 10 than location 150, the unchanged angle associated with the ROI results in a larger ROI 142 (shown in dashed lines). The larger ROI 142 encompasses a larger region of the forehead of patient 2, while the changed angle associated with the ROI based on the distance between patient 2 and thermal camera 10 (or depth camera 8), results in ROI 144 which remains at or about the same size as ROI 140 relative to the forehead of patient 2.

When patient 2 moves even further from thermal camera 10 to location 154, the unchanged angle associated with the ROI results in ROI 146 (shown in dashed lines) encompassing an even larger area of the forehead of patient 2 than ROI 140, 142, 144, e.g., even impinges on the eyes of patient 2, while the changed angle associated with the ROI based on the distance between patient 2 and thermal camera 10 (or depth camera 8) results in ROI 148 which remains at or about the same size relative as ROI 140 to the forehead of patient 2. Thus, changing the angle associated with the ROI based on the distance between patient 2 and thermal camera 10 (or depth camera 8) results in a fixed ROI (solid lines) that covers roughly the same area of the face of patient 2 irrespective of distance as shown in FIG. 15. However, not changing the angle associated with the ROI based on the distance between patient 2 and thermal camera 10 results in a changing ROI (dashed lines) that covers an increasingly larger area of patient 2's face as the distance from thermal camera 10 increases.

In some examples, processing circuitry 200 modifies an angle associated with the ROI based on a distance between patient 2 and thermal camera 10, e.g., determined using depth camera 8 or another depth camera, to scale the ROI based on distance. Scaling the ROI in this manner may help a measure of a core temperature determined based on a thermal image captured by thermal camera 10 be more consistent over time, despite patient 2 moving closer or further from thermal camera 10. For example, processing circuitry 200 of computing device 14 may at a first time, via depth camera 8, determine a first distance L1 between at least one of depth camera 8 or the thermal camera 10 and patient 2. Processing circuitry 200 may control a first angle associated with the ROI (e.g., angle θ) based on the first distance L1. Processing circuitry 200 may acquire, via thermal camera 10, a first thermal image associated with patient 2. Processing circuitry 200 may determine, based on the thermal image, a first sensed temperature of a location associated with patient 2. For example, the location associated with patient 2 may be a location on the face of patient 2, a location on clothing contacting patient 2, a location on a blanked contacting patient 2, or a location on bed linens contacting patient 2. At a second time different than the first time, processing circuitry 200 may determine a second distance L2 between at least one of depth camera 8 or thermal camera 10 and patient 2 and may control a second angle associated with the ROI (e.g., θ×(L1/L2)) based on the second distance. Processing circuitry 200 may acquire, via thermal camera 10, a second thermal image associated with the patient and determine, based on the second thermal image, a second sensed temperature of the location. For example, if patient 2 is 2 meters from thermal camera 10 and the ROI width is 2 centimeters, then the angle associated with the ROI is θ=2 arctan(1/200)=0.57 degrees. When patient 2 moves to 4 meters from thermal camera 10, processing circuitry 200 may control thermal camera 10 to change the angle associated with the ROI to be half of what the angle associated with the ROI was when the patient was 2 meters from thermal camera 10 of 0.285 degrees to keep the ROI the same size.

In some examples, processing circuitry 200 may acquire a reference temperature of patient 2. Processing circuitry 200 may determine a reference temperature delta between the reference temperature and a first sensed temperature. Processing circuitry 200 of computing device 14 may determine, based on the reference temperature delta, a measure of a temperature at a second location, the second location being different than the first location. In some examples, the second location is the core of patient 2. In some examples, the second location is a location on one of the face of the patient, clothing contacting the patient, a blanket contacting the patient, or bed linens contacting the patient.

Figure 16:
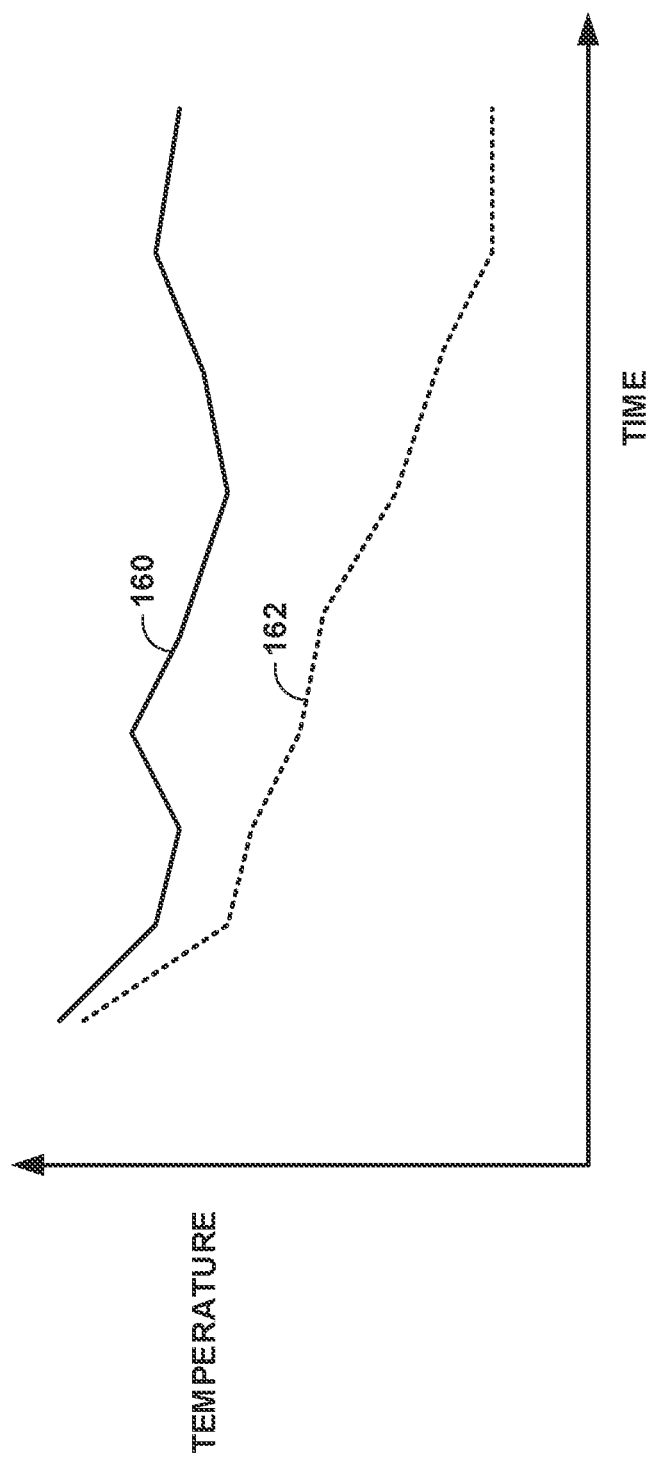
FIG. 16 is a graph illustrating example ROI temperatures sensed using the fixed and scaled ROIs shown in FIG. 14.

FIG. 16 is a graph illustrating example ROI temperatures sensed using the fixed and changing ROIs shown in FIG. 16. In this example, it can be seen that for the fixed ROI line 160, the temperature decreases much less as the distance between patient 2 and thermal camera 10 increases. For the changing ROI line 162, the average temperature drops significantly more as the distance between patient 2 and thermal camera 10 increases. This significant drop may be due to processing circuitry 200 determining the mean, median, or mode of the sensed temperature over a different region of the face of patient 2 at each distance. For example, for some locations, the difference in the reduction in temperature may be due to the ROI pulling parts of the nose, which may be much cooler than the forehead. This shows the less stable nature of not changing the angle associated with the based on the distance between thermal camera 10 (or depth camera 8) and patient 2.

In other examples, another camera 15, such as a red green blue (RGB) camera or any other camera (for example, an infrared (IR) camera) or computing device 14 via another camera 15 may extract distinct features on for example, the head of patient 2. These features (e.g., at least two) may be, for example, eyes, an eye and nose, etc. the distance between the eyes, between the eyes and nose, and the like. Processing circuitry 200 may determine the distances between the features, such as the distance between the eyes, between the eyes and nose, and the like. When patient 2 moves to a different location, an angle associated with the distance between the features may change. Processing circuitry 200 may use the distance between features on the head of patient 2 as a reference to control thermal camera 10 to change the angle associated with the ROI so that the ROI size remains the same for different distances of L. In some examples, processing circuitry 200 of computing device 14 may use this technique as a double check on the ROI determined through the use of depth camera 8. For example, processing circuitry 200 may determine a plurality of features of the face of patient 2 based on an image captured by another camera 15, such as the eyes of patient 2. Processing circuitry 200 may determine a distance between the eyes of patient 2.

Processing circuitry 200 may determine the first angle associated with the ROI and a second angle associated with the ROI as discussed above further based on the plurality of features (e.g., the eyes of patient 2 and more specifically, the known distance between the eyes of patient 2).

Figure 17:
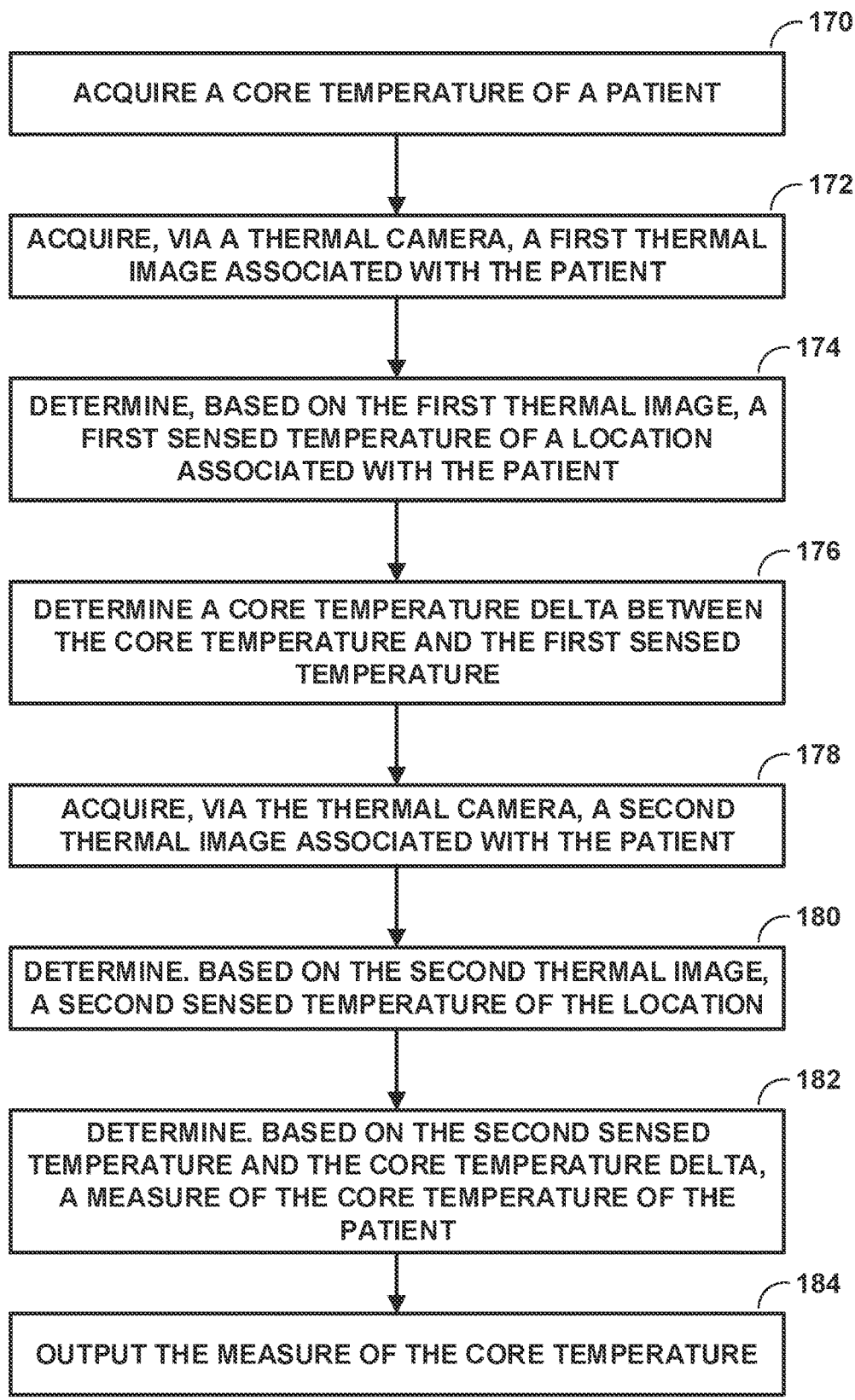
FIG. 17 is a flowchart illustrating an example temperature monitoring technique.

FIG. 17 is a flowchart illustrating an example temperature monitoring technique. For example, processing circuitry 200 of computing device 14 may acquire a core temperature of patient 2 (170). For example, a clinician may take a core temperature of patient 2 and enter the actual core temperature into UI 204 of computing device 14 or via communication circuitry 206, or a patient monitoring device may automatically provide the actual core temperature to processing circuitry 200. Processing circuitry 200 may acquire, via thermal camera 10, a first thermal image associated with patient 2 (172). For example, processing circuitry 200 may control thermal camera 10 to take a first thermal image of the face of patient 2, exposed skin of patient 2, clothing 68 contacting patient 2, blanket 70 contacting patient 2 or bed linens contacting patient 2. Thermal camera 10 may provide the first thermal image to computing device 14 via communication circuitry 206. Processing circuitry 200 may store the thermal image in thermal images 212 of memory 202.

Processing circuitry 200 may determine, based on the first thermal image, a first sensed temperature of a location associated with the patient (174). For example, processing circuitry 200 may analyze the first thermal image to determine the first sensed temperature. In some examples, the location associated with the patient is a point associated with patient 2. In other examples, the location is an ROI associated with patient 2. For example, processing circuitry 200 may determine a first sensed temperature of location 4, location 6, location 12, (FIG. 1) or any other location associated with patient 2. Processing circuitry 200 may determine a core temperature delta between the actual core temperature and the first sensed temperature (176). For example, processing circuitry 200 may subtract one of the first sensed temperature or the actual core temperature from the other of the first sensed temperature or the core temperature to determine the core temperature delta. Processing circuitry 200 may store the core temperature delta in reference temperature deltas 214 of memory 202.

Processing circuitry 200 may acquire, via thermal camera 10 a second thermal image associated with patient 2 (178). For example, processing circuitry 200 may control thermal camera 10 to take a second thermal image of the face of patient 2, exposed skin of patient 2, clothing 68 contacting patient 2, blanket 70 contacting patient 2 or bed linens contacting patient 2. Thermal camera 10 may provide the second thermal image to computing device 14 via communication circuitry 206. Processing circuitry 200 may store the second thermal image in thermal images 212 of memory 202. Processing circuitry 200 may determine, based on the second thermal image, a second sensed temperature of the location (180). For example, processing circuitry 200 may determine a second sensed temperature of location 4, location 6, location 12, or any other location associated with patient 2.

Processing circuitry 200 may determine a measure of the core temperature of patient 2 based on the second sensed temperature and the core temperature delta (182). For example, processing circuitry 200 may add or subtract the core temperature delta to or from the second sensed temperature to determine the measure of the core temperature of patient 2. Processing circuitry 200 may output the measure of the core temperature (184), e.g., via display 210, speaker 216, UI 204, or communication circuitry 206. For example, computing device 14 may transmit the measure of the core temperature to another device, such as a nurses' station or may display the measure of the core temperature on a display. In some examples, in response to determining the measure of the core temperature of patient 2 is greater than or equal to a predetermined threshold, processing circuitry 200 may send an alert via display 210, speaker 216, UI 204, or communication circuitry 206 to a clinician. The predetermined threshold can be stored by memory 202 of computing device 14 or a memory of another device.

In some examples, processing circuitry 200 may also take into account other factors when calibrating or estimating a core temperature of patient 2. These techniques may be used with any other techniques of this disclosure. The other factors may include environmental factors and/or physiological factors that may impact the core temperature of patient 2, e.g., over time or between patients. For example, such environmental factors may include air temperature, air humidity, presence of blanket 70 or other bed linens on patient 2, air flow circulation/draughts in the immediate area of patient 2, the use of a heated blanket, and the like. Example physiological factors may include patient metrics such as height, weight, body mass index (BMI), skin pigmentation, prior patient activity, fluid intake, and the like. In some examples, processing circuitry 200 may take disease state or illness of patient (e.g., fever) into account when determining a measure of a core temperature of patient 2. For example, processing circuitry 200 may determine additional temperature deltas based on environmental factors or physiological factors and may add or subtract the additional temperature deltas to or from a sensed temperature.

In some examples, processing circuitry 200 may determine, in response to patient 2 moving, based on the temperature map of the face of the patient, a face temperature delta between a first location on the face of the patient and a second location on the face of the patient and determine, based on the face temperature delta and a sensed temperature at the second location, a measure of a temperature at the first location.

In some examples, the measure of the core temperature is a first measure of the core temperature and processing circuitry 200 may determine, based on the measure of the temperature at a first location on the face of the patient and the core temperature delta, a second measure of the core temperature. Processing circuitry 200 may output the second measure of the core temperature.

Figure 18:
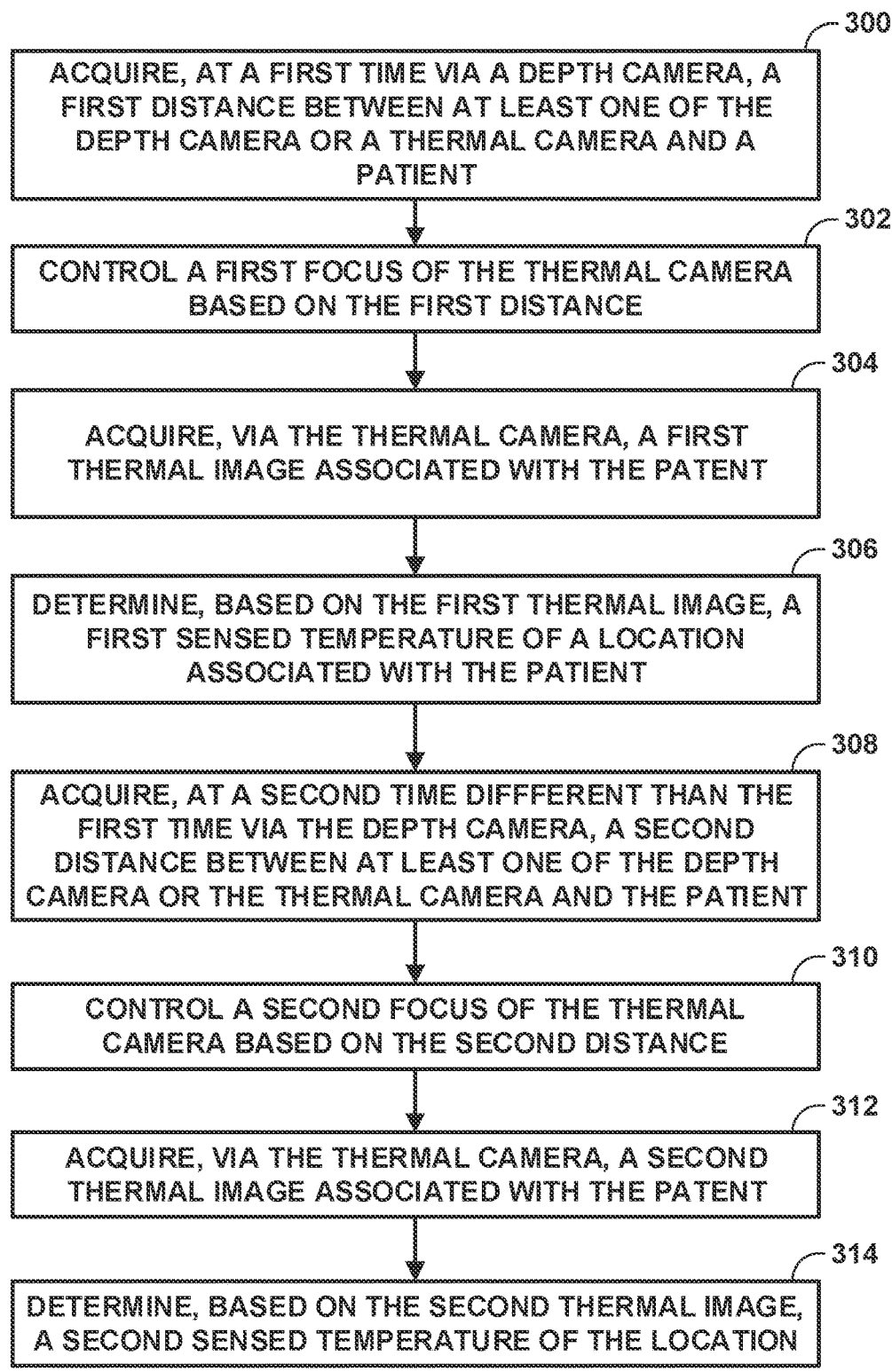
FIG. 18 is a flowchart illustrating another example temperature monitoring technique.

FIG. 18 is a flowchart illustrating another example temperature monitoring technique. Processing circuitry 200 may acquire, at a first time via a depth camera, a first distance between at least one of the depth camera or a thermal camera and a patient (300). For example, processing circuitry 200 may acquire from depth camera 8 a first distance between depth camera 8 or thermal camera 10 and patient 2. For example, processing circuitry 200 may acquire L1 (FIG. 14) from depth camera 8. Processing circuitry 200 may control a first angle associated with an ROI based on the first distance (302). For example, processing circuitry 200 may control a first angle θ which is based on the first distance L1. For example, the first angle θ may be determined based on the first distance L1 such that a ROI is of a desired size or the ROI or point is at a desired location.

Processing circuitry 200 may acquire, via the thermal camera, a first thermal image associated with the patient (304). For example, processing circuitry 200 may control thermal camera 10 to take a first thermal image associated with the patient (e.g., a thermal image of the ROI or point) and may acquire the first thermal image from thermal camera 10 via communication circuitry 206. Processing circuitry 200 may determine, based on the first thermal image, a first sensed temperature of a location associated with the patient (306). For example, processing circuitry 200 may analyze the first thermal image to determine the first sensed temperature. In some examples, the location associated with the patient is a point associated with patient 2. In other examples, the location is an ROI region of interest associated with patient 2. For example, processing circuitry 200 may determine a first sensed temperature of location 4, location 6, location 12, (FIG. 1) or any other location associated with patient 2.

Processing circuitry 200 may acquire, at a second time different than the first time via the depth camera, a second distance between at least one of the depth camera or the thermal camera and the patient (308). For example, processing circuitry 200 may acquire from depth camera 8 a second distance between depth camera 8 or thermal camera 10 and patient 2. For example, processing circuitry 200 may acquire L2 (FIG. 14) from depth camera 8. Processing circuitry 200 may control a second angle associated with the ROI based on the second distance (310). For example, processing circuitry 200 may control a second angle associated with the ROI $\theta \times (L1/L2)$ which is based on the second distance L2. For example, the second angle $\theta \times (L1/L2)$ may be determined such that a ROI is of a same size or focused on the same location as when patient 2 was at distance L1 from depth camera 8 or thermal camera 10.

Processing circuitry 200 may acquire, via the thermal camera, a second thermal image associated with the patient (312). For example, processing circuitry 200 may control thermal camera 10 to take a second thermal image associated with the patient (e.g., a thermal image of the ROI or point) and may acquire the second thermal image from thermal camera 10 via communication circuitry 206. Processing circuitry 200 may determine, based on the second thermal image, a second sensed temperature of the location (314). For example, processing circuitry 200 may analyze the second thermal image to determine the second sensed temperature of the location.

In some examples, the location is a first location and processing circuitry 200 may acquire a reference temperature of the patient. In some examples, processing circuitry 200 may determine a reference temperature delta between the reference temperature and the first sensed temperature. In some examples, processing circuitry may determine, based on the reference temperature delta, a measure of a temperature at a second location, the second location being different than the first location. In some examples, the second location is a core of the patient.

In some examples, processing circuitry 200 may determine a plurality of features on the face of patient 2 based on an image captured by another camera. Processing circuitry 200 may determine a distance between the plurality of features. Processing circuitry 200 may use the distance between the plurality of features as a reference to control the angle associated with the ROI, such that the first angle associated with the ROI and the second angle associated with the ROI are based on or further based on the plurality of features Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including a thermal camera, a computing device, a depth camera, a RGB camera, any other camera, or any combination of such devices or apparatuses, an integrated circuit (IC) or a set of ICs, and/or discrete electrical circuitry, residing in any such devices or apparatuses.

This disclosure includes the following examples.

Example 1. A system comprising: a thermal camera; a memory; and processing circuitry coupled to the thermal camera and the memory, the processing circuitry being configured to: acquire a core temperature of a patient; acquire, via the thermal camera, a first thermal image associated with a patient; determine, based on the first thermal image, a first sensed temperature of a location associated with the patient; determine a core temperature delta between the core temperature and the first sensed temperature; acquire, via the thermal camera, a second thermal image associated with a patient; determine, based on the second thermal image, a second sensed temperature of the location; determine, based on the second sensed temperature and the core temperature delta, a measure of the core temperature; and output the measure of the core temperature.

Example 2. The system of example 1, wherein the location is a point associated with the patient.

Example 3. The system of example 1, wherein the location is a region of interest associated with the patient.

Example 4. The system of any combination of example 1 or 2, or example 1 or 3, wherein the location is on one of a face of the patient, clothing contacting the patient, a blanket contacting the patient, or bed linens contacting the patient.

Example 5. The system of any combination of example 1 or 4, wherein the processing circuitry is further configured to: determine, based on the first thermal image, a temperature map of a face of the patient.

Example 6. The system of example 5, wherein the processing circuitry is further configured to: determine, in response to the patient moving and based on the temperature map of the face of the patient, a face temperature delta between a first location on the face of the patient and a second location on the face of the patient; and determine, based on the face temperature delta and a sensed temperature at the second location based on the second thermal image, a measure of a temperature at the first location.

Example 7. The system of example 6, wherein the measure of the core temperature is a first measure of the core temperature, wherein the processing circuitry is further configured to: determine, based on the measure of the temperature at the first location on the face of the patient and the core temperature delta, a second measure of the core temperature; and output the second measure of the core temperature.

Example 8. The system of any combination of examples 1-7, further comprising a depth camera, wherein the processing circuitry is further configured to: at a first time, acquire a first distance between at least one of the depth camera or the thermal camera and the patient; control a first angle associated with a region of interest (ROI) based on the first distance; at a second time different than the first time, acquire a second distance between at least one of the depth camera or the thermal camera and the patient; and control a second angle associated with the ROI based on the first distance and the second distance, wherein the first distance is different than the second distance and the first angle is different than the second angle.

Example 9. The system of example 8, further comprising another camera, wherein the processing circuitry is further configured to: determine a plurality of features of a face of the patient based on an image captured by the another camera, and wherein the first angle and the second angle are further based on the plurality of features.

Example 10. The system of any combination of examples 1-9, wherein the processing circuitry is further configured to: determine an additional temperature delta; and determine, based on the additional temperature delta, the second sensed temperature, and the core temperature delta, the measure of the core temperature, wherein the additional temperature delta is based on at least one of an environmental factor or a physiological factor of the patient.

Example 11. A method comprising: acquiring, by processing circuitry, a core temperature of a patient; acquiring, by the processing circuitry, a first thermal image associated with the patient; determining, by the processing circuitry and based on the first thermal image, a first sensed temperature of a location associated with the patient; determining, by the processing circuitry, a core temperature delta between the core temperature and the first sensed temperature; acquiring, by the processing circuitry, a second thermal image associated with the patient; determining, by the processing circuitry and based on the second thermal image, a second sensed temperature of the location; determining, by the processing circuitry and based on the second sensed temperature and the core temperature delta, a measure of the core temperature; and outputting the measure of the core temperature.

Example 12. The method of example 11, wherein the location is a point associated with the patient.

Example 13. The method of example 11, wherein the location is a region of interest associated with the patient.

Example 14. The method of any combination of example 11 or 12, or example 11 or 13, wherein the location is on one of a face of the patient, clothing contacting the patient, a blanket contacting the patient, or bed linens contacting the patient.

Example 15. The method of any combination of example 11-14, further comprising:
determining, by the processing circuitry and based on the first thermal image, a temperature map of a face of the patient.

Example 16. The method of example 15, further comprising: determining, in response to the patient moving, by the processing circuitry and based on the temperature map of the face of the patient, a face temperature delta between a first location on the face of the patient and a second location on the face of the patient; and determining, by the processing circuitry and based on the face temperature delta and a sensed temperature at the second location, a measure of a temperature at the first location.

Example 17. The method of example 16, wherein the measure of the core temperature is a first measure of the core temperature, further comprising: determining, by the processing circuitry and based on the measure of the temperature at the first location on the face of the patient and the core temperature delta, a second measure of the core temperature; and outputting the second measure of the core temperature.

Example 18. The method of any combination of examples 11-17, further comprising: acquiring at a first time, by the processing circuitry, a first distance between at least one of a depth camera or a thermal camera and the patient; controlling, by the processing circuitry, a first angle of the thermal camera based on the first distance; acquiring at a second time different than the first time, by the processing circuitry, a second distance between at least one of the depth camera or the thermal camera and the patient; and controlling, by the processing circuitry, a second angle of the thermal camera based on the first distance and the second distance, wherein the first distance is different than the second distance and the first angle is different than the second angle.

Example 19. The method of example 18, further comprising: determining, by the processing circuitry, a plurality of features of a face of the patient, wherein the first angle and the second angle are further based on the plurality of features.

Example 20. The method of any combination of examples 11-19, wherein the determining the measure of the core temperature is continuous.

Example 21. A system comprising: a thermal camera; a depth camera; a memory; and processing circuitry coupled to the thermal camera, the depth camera, and the memory, the processing circuitry being configured to: at a first time, via the depth camera, acquire a first distance between at least one of the depth camera or the thermal camera and a patient; control a first angle associated with a region of interest (ROI) based on the first distance; acquire, via the thermal camera, a first thermal image associated with the patient; determine, based on the first thermal image, a first sensed temperature of a location associated with the patient; acquire, at a second time different than the first time via the depth camera, a second distance between at least one of the depth camera or the thermal camera and the patient; control a second angle associated with the ROI based on the second distance; acquire, via the thermal camera, a second thermal image associated with the patient; and determine, based on the second thermal image, a second sensed temperature of the location.

Example 22. The system of example 21, wherein the location is a first location and the processing circuitry is further configured to: acquire a reference temperature of the patient; determine a reference temperature delta between the reference temperature and the first sensed temperature;

determine, based on the reference temperature delta, a measure of a temperature at a second location, the second location being different than the first location.

Example 23. The system of example 22, wherein the second location is a core of the patient.

Example 24. The system of any combination of examples 21 or 22, wherein the second location is a location on one of a face of the patient, clothing contacting the patient, a blanket contacting the patient, or bed linens contacting the patient.

Example 25. The system of any combination of examples 21-23, wherein the processing circuitry is further configured to: determine a plurality of features of a face of the patient based on an image captured by another camera, and wherein the first angle and the second angle are further based on the plurality of features.

Example 26. A method comprising: acquiring, by processing circuitry at a first time via a depth camera, a first distance between at least one of the depth camera or a thermal camera and a patient; controlling, by the processing circuitry, a first angle associated with a region of interest (ROI) based on the first distance; acquiring, by the processing circuitry via the thermal camera, a first thermal image associated with the patient; determining, by the processing circuitry and based on the first thermal image, a first sensed temperature of a location associated with the patient; acquiring, by the processing circuitry at a second time different than the first time, a second distance between at least one of the depth camera or the thermal camera and the patient; controlling, by the processing circuitry, a second angle associated with the ROI based on the second distance; acquiring, by the processing circuitry via the thermal camera, a second thermal image associated with the patient; and determining, by the processing circuitry and based on the second thermal image, a second sensed temperature of the location.

Example 27. The method of example 26, wherein the location is a first location, further comprising: acquiring, by the processing circuitry, a reference temperature of the patient; determining, by the processing circuitry, a reference temperature delta between the reference temperature and the first sensed temperature; determining, by the processing circuitry and based on the reference temperature delta, a measure of a temperature at a second location, the second location being different than the first location.

Example 28. The method of example 27, wherein the second location is a core of the patient.

Various aspects of the disclosure have been described. These and other aspects are within the scope of the following claims.

What is claimed is:

1. A system comprising:
   a thermal camera;
   a depth camera;
   a memory; and
   processing circuitry coupled to the thermal camera, the depth camera, and the memory, the processing circuitry being configured to:
   at a first time, via the depth camera, acquire a first distance between at least one of the depth camera or the thermal camera and a patient;
   control a first angle associated with a region of interest (ROI) based on the first distance;
   acquire, via the thermal camera, a first thermal image associated with the patient;
   determine, based on the first thermal image, a first sensed temperature of a location associated with the patient;
   acquire, at a second time different than the first time via the depth camera, a second distance between at least one of the depth camera or the thermal camera and the patient;
   control a second angle associated with the ROI based on the second distance;
   acquire, via the thermal camera, a second thermal image associated with the patient; and
   determine, based on the second thermal image, a second sensed temperature of the location.

2. The system of claim 1, wherein the location is a first location and the processing circuitry is further configured to:
   acquire a reference temperature of the patient;
   determine a reference temperature delta between the reference temperature and the first sensed temperature;
   determine, based on the reference temperature delta, a measure of a temperature at a second location, the second location being different than the first location.

3. The system of claim 2, wherein the second location is a core of the patient.

4. The system of claim 2, wherein the second location is a location on one of a face of the patient, clothing contacting the patient, a blanket contacting the patient, or bed linens contacting the patient.

5. The system of claim 1, wherein the processing circuitry is further configured to:
   determine a plurality of features of a face of the patient based on an image captured by another camera, and
   wherein the first angle and the second angle are further based on the plurality of features.

6. A method comprising:
   acquiring, by processing circuitry at a first time via a depth camera, a first distance between at least one of the depth camera or a thermal camera and a patient;
   controlling, by the processing circuitry, a first angle associated with a region of interest (ROI) based on the first distance;
   acquiring, by the processing circuitry via the thermal camera, a first thermal image associated with the patient;
   determining, by the processing circuitry and based on the first thermal image, a first sensed temperature of a location associated with the patient;
   acquiring, by the processing circuitry at a second time different than the first time, a second distance between at least one of the depth camera or the thermal camera and the patient;
   controlling, by the processing circuitry, a second angle associated with the ROI based on the second distance;
   acquiring, by the processing circuitry via the thermal camera, a second thermal image associated with the patient; and
   determining, by the processing circuitry and based on the second thermal image, a second sensed temperature of the location.

7. The method of claim 6, wherein the location is a first location, further comprising:
   acquiring, by the processing circuitry, a reference temperature of the patient;
   determining, by the processing circuitry, a reference temperature delta between the reference temperature and the first sensed temperature;

determining, by the processing circuitry and based on the reference temperature delta, a measure of a temperature at a second location, the second location being different than the first location.

8. The method of claim 7, wherein the second location is a core of the patient.

9. The method of claim 7, wherein the second location is a location on one of a face of the patient, clothing contacting the patient, a blanket contacting the patient, or bed linens contacting the patient.

10. The method of claim 6, further comprising:
determining, by the processing circuitry, a plurality of features of a face of the patient based on an image captured by another camera,
wherein the first angle and the second angle are further based on the plurality of features.

* * * * *